US009895162B2

(12) United States Patent
Anderson et al.

(10) Patent No.: US 9,895,162 B2
(45) Date of Patent: Feb. 20, 2018

(54) METHOD AND APPARATUS FOR TISSUE GRAFTING AND COPYING

(71) Applicant: The General Hospital Corporation, Boston, MA (US)

(72) Inventors: Richard Rox Anderson, Boston, MA (US); William A. Farinelli, Danvers, MA (US); Walfre Franco, Worcester, MA (US); Joshua Tam, Charlestown, MA (US); Fernanda H. Sakamoto, Boston, MA (US); Apostolos G. Doukas, Belmont, MA (US); Martin Purschke, Dorchester, MA (US); Min Yao, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 350 days.

(21) Appl. No.: 14/711,936

(22) Filed: May 14, 2015

(65) Prior Publication Data

US 2015/0238214 A1    Aug. 27, 2015

Related U.S. Application Data

(62) Division of application No. 13/102,711, filed on May 6, 2011, now Pat. No. 9,060,803.
(Continued)

(51) Int. Cl.
*A61B 17/322* (2006.01)
*A61B 10/02* (2006.01)
(Continued)

(52) U.S. Cl.
CPC ........ *A61B 17/322* (2013.01); *A61B 10/0233* (2013.01); *A61B 17/3205* (2013.01);
(Continued)

(58) Field of Classification Search
CPC ...... A61B 17/3205; A61B 2017/00747; A61B 2017/00969
(Continued)

(56) References Cited

U.S. PATENT DOCUMENTS 2,426,535 A    8/1947  Turkel
3,598,108 A    8/1971  Jamshidi et al.
(Continued)

FOREIGN PATENT DOCUMENTS

CN    2126570 Y    1/1993
CN    1115629 A    1/1996
(Continued)

OTHER PUBLICATIONS

Alsberg, E., et al., "Engineering growing tissues," PNAS, vol. 99, No. 19, pp. 12025-12030 (Sep. 17, 2002).
(Continued)

*Primary Examiner* — David C Eastwood
(74) *Attorney, Agent, or Firm* — Wilmer Cutler Pickering Hale and Dorr LLP

(57) ABSTRACT

Exemplary embodiments of apparatus and method for obtaining one or more portions of biological tissue ("micrografts") to form grafts are provided. For example, a hollow tube can be inserted into tissue at a donor site, and a pin provided within the tube can facilitate controlled removal of the micrograft from the tube. Micrografts can be harvested and directly implanted into an overlying biocompatible matrix through coordinated motion of the tube and pin. A needle can be provided around the tube to facilitate a direct implantation of a micrograft into a remote recipient site or matrix. The exemplary apparatus can include a plurality of such tubes and pins for simultaneous harvesting and/or implanting of a plurality of micrografts. The harvested micrografts can have a small dimension, e.g., less than about
(Continued)

1 mm, which can promote healing of the donor site and/or viability of the harvested tissue.

3 Claims, 15 Drawing Sheets

Related U.S. Application Data

(60) Provisional application No. 61/332,230, filed on May 7, 2010, provisional application No. 61/373,498, filed on Aug. 13, 2010, provisional application No. 61/437,507, filed on Jan. 28, 2011.

(51) Int. Cl.
    *A61B 17/3205*     (2006.01)
    *A61B 17/00*     (2006.01)

(52) U.S. Cl.
    CPC .......... *A61B 17/32053* (2013.01); *A61B 2017/00747* (2013.01); *A61B 2017/00752* (2013.01); *A61B 2017/00969* (2013.01); *A61B 2017/3225* (2013.01)

(58) Field of Classification Search
    USPC ............. 606/131–133, 167, 170, 172, 180, 606/184–187; 600/36, 562, 564, 567, 600/568; 604/22, 27, 57, 59, 60; 623/15.11, 15.12, 915, 920; 422/50, 129, 422/211, 213, 219, 232, 243, 292, 922, 422/935, 936; 424/400, 422, 423; 436/807; 435/283.1, 286.1, 286.2, 286.5, 435/290.4, 293.1, 293.2, 297.4, 298.1, 435/299.1, 309.1; 514/946
    See application file for complete search history.

(56) References Cited

U.S. PATENT DOCUMENTS

| | | | |
|---|---|---|---|
| 3,788,320 A | 1/1974 | Dye | |
| 4,403,617 A | 9/1983 | Tretinyak | |
| 4,458,678 A | 7/1984 | Yannas et al. | |
| 4,476,864 A | 10/1984 | Tezel | |
| 4,604,346 A | 8/1986 | Bell et al. | |
| 4,640,296 A | 2/1987 | Schnepp-Pesch et al. | |
| 5,152,763 A | 10/1992 | Johnson | |
| 5,331,972 A | 7/1994 | Wadhwani et al. | |
| 5,415,182 A | 5/1995 | Chin et al. | |
| 5,439,475 A | 8/1995 | Bennett | |
| 5,611,810 A | 3/1997 | Arnold et al. | |
| 5,639,654 A | 6/1997 | Bernard et al. | |
| 5,792,169 A | 8/1998 | Markman | |
| 5,827,297 A | 10/1998 | Boudjema | |
| 5,885,226 A | 3/1999 | Rubinstein et al. | |
| 5,922,000 A | 7/1999 | Chodorow | |
| 5,928,162 A | 7/1999 | Giurtino et al. | |
| 6,059,807 A | 5/2000 | Boudjema | |
| 6,440,086 B1 | 8/2002 | Hohenberg | |
| 6,997,923 B2 | 2/2006 | Anderson et al. | |
| 7,073,510 B2 | 7/2006 | Redmond et al. | |
| 7,651,507 B2 | 1/2010 | Mishra et al. | |
| 7,926,401 B2 | 4/2011 | Mishra et al. | |
| 8,226,664 B2 | 7/2012 | Drews et al. | |
| 8,696,686 B2 | 4/2014 | Drews et al. | |
| 9,017,343 B2 | 4/2015 | Westerling, Jr. et al. | |
| 9,060,803 B2 | 6/2015 | Anderson et al. | |
| 9,084,465 B2 | 7/2015 | Oostman, Jr. et al. | |
| 9,119,945 B2 | 9/2015 | Simons et al. | |
| 2002/0103500 A1 | 8/2002 | Gildenberg | |
| 2003/0195625 A1 | 10/2003 | Garcia Castro et al. | |
| 2004/0002723 A1 | 1/2004 | Ball | |
| 2004/0054410 A1 | 3/2004 | Barrows | |
| 2005/0143713 A1 | 6/2005 | Delmore et al. | |
| 2005/0226856 A1 | 10/2005 | Ahlfors | |
| 2006/0155266 A1 | 7/2006 | Manstein et al. | |
| 2006/0216781 A1 | 9/2006 | Gebing | |
| 2007/0038236 A1 | 2/2007 | Cohen | |
| 2007/0073327 A1 | 3/2007 | Giovannoli | |
| 2007/0106306 A1 | 5/2007 | Bodduluri et al. | |
| 2007/0142744 A1 | 6/2007 | Provencher | |
| 2007/0270710 A1 | 11/2007 | Frass et al. | |
| 2008/0045861 A1 | 2/2008 | Miller et al. | |
| 2008/0208146 A1 | 8/2008 | Brandwein et al. | |
| 2009/0146068 A1 | 6/2009 | Agarwal | |
| 2009/0198336 A1 | 8/2009 | Qiao et al. | |
| 2010/0041938 A1 | 2/2010 | Stoianovici et al. | |
| 2012/0041430 A1 | 2/2012 | Anderson et al. | |
| 2012/0271320 A1 | 10/2012 | Hall et al. | |
| 2014/0200484 A1 | 7/2014 | Austen et al. | |
| 2015/0238214 A1 | 8/2015 | Anderson et al. | |
| 2015/0258319 A1 | 9/2015 | Simmers | |
| 2015/0320990 A1 | 11/2015 | Burton et al. | |
| 2016/0082241 A1 | 3/2016 | Burton et al. | |
| 2016/0121091 A1 | 5/2016 | Burton et al. | |
| 2016/0136406 A1 | 5/2016 | Berry et al. | |

FOREIGN PATENT DOCUMENTS

| | | |
|---|---|---|
| CN | 101128156 A | 2/2008 |
| CN | 101277657 A | 12/2010 |
| DE | 287651 A5 | 3/1991 |
| JP | 57-163208 A | 10/1982 |
| JP | 07-100140 | 4/1995 |
| JP | 10-000210 | 1/1998 |
| JP | 2000-139929 A | 5/2000 |
| JP | 2002-505605 A | 2/2002 |
| JP | 2007-041267 A | 2/2007 |
| JP | 2008-036393 A | 2/2008 |
| JP | 2009-509671 A | 3/2009 |
| JP | 2011516169 A | 5/2011 |
| KR | 10-2008-0049793 | 6/2008 |
| TW | 402497 B | 8/2000 |
| WO | WO-1995/28896 A1 | 11/1995 |
| WO | WO-9718758 A1 | 5/1997 |
| WO | WO-02096321 A1 | 12/2002 |
| WO | WO-2005/013830 A1 | 2/2005 |
| WO | WO-2005072181 A2 | 8/2005 |
| WO | WO-2005/109799 A2 | 11/2005 |
| WO | WO-2007/041267 A2 | 4/2007 |
| WO | WO-2008/033873 A2 | 3/2008 |
| WO | WO-2009/146068 A1 | 12/2009 |

OTHER PUBLICATIONS

Australian Examination Report issued by the Australian Intellectual Property Office for Australian Application No. 2009251617 dated Jul. 19, 2013 (15 pages).

Chinese Office Action issued by the State Intellectual Property Office for the People's Republic of China for Chinese Application No. 200980120442.7 dated Dec. 31, 2012 (12 pages).

International Search Report and Written Opinion issued by the Korean Intellectual Property Office as International Searching Authority for International Application No. PCT/US2009/039114 dated Nov. 16, 2009 (10 pages).

International Search Report and Written Opinion issued by the U.S. Patent and Trademark Office as International Search Authority for International Application No. PCT/US2011/035613 dated May 6, 2011 (8 pages).

International Searching Report and Written Opinion issued by the Korean Intellectual Property Office as International Searching Authority for International Application No. PCT/US2011/035613 dated Jan. 12, 2012 (6 pages).

Japanese First Office Action issued by the Japan Patent Office for Japanese Application No. 2011-503136 dated Jun. 17, 2013 (13 pages).

Final Office Action for U.S. Appl. No. 13/102,711 dated Jul. 19, 2013 (14 pages).

Non-Final Office Action issued by the U.S. Patent and Trademark Office for U.S. Appl. No. 12/936,173 dated Apr. 10, 2013 (15 pages).

(56) References Cited

OTHER PUBLICATIONS

Non-Final Office Action for U.S. Appl. No. 13/102,711 dated Nov. 13, 2012 (13 pages).
Office Action issued by the U.S. Patent and Trademark Office for U.S. Appl. No. 12/936,173 dated Feb. 7, 2013 (9 pages).
Response filed for Chinese Application No. 200980120442.7 filed on Jul. 28, 2014 (4 pages).
Moore, J. Z., et al., "Modeling of the Plane Needle Cutting Edge Rake and Inclination Angles for Biopsy," Journal of Manufacturing Science and Engineering, vol. 132, pp. 015001-5-015001-8 (Oct. 2010).
Notice of Rejection issued by the Japan Patent Office for Japanese Application No. 2013-509310 dated Dec. 2, 2014 (7 pages).
Supplementary European Search Report issued by the European Patent Office for Application No. 11778450.4 dated Jan. 27, 2015 (5 pages).
Third Chinese Office Action and Supplemental Search Report issued by the State Intellectual Property Office for the People's Republic of China for Chinese Application No. 200980120442.7 dated May 12, 2014 (12 pages).
Third Office Action issued by the State Intellectual Property Office of People's Republic of China for Chinese Application No. 201180028199.3 dated Nov. 6, 2015 (18 pages).

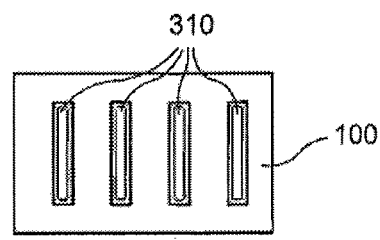
FIG. 3A
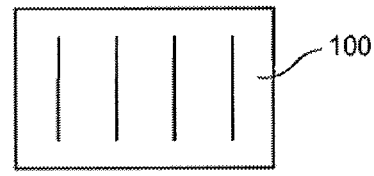
FIG. 3B
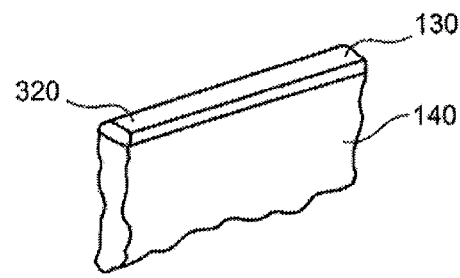
FIG. 3C
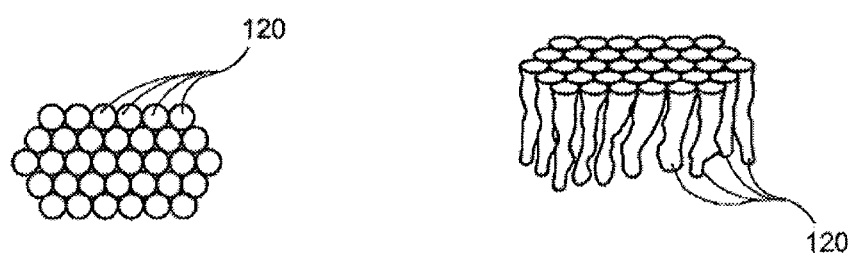
FIG. 4A
FIG. 4B

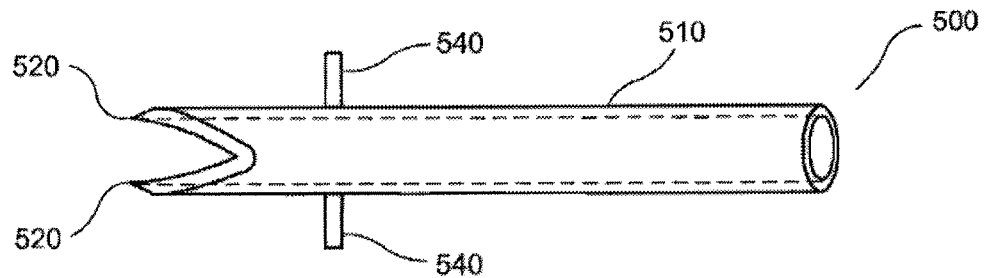
FIG. 5A
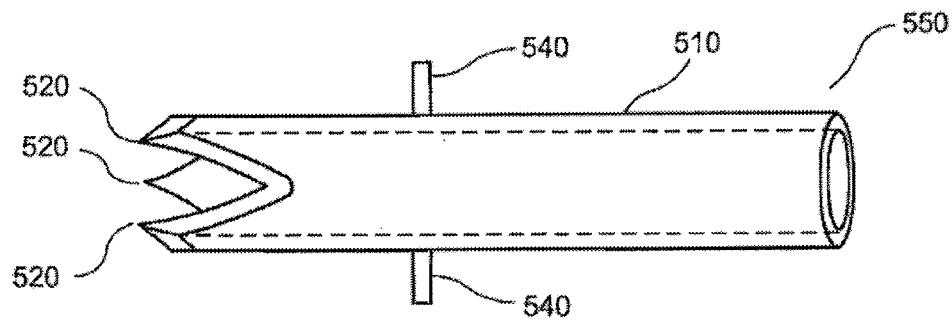
FIG. 5B
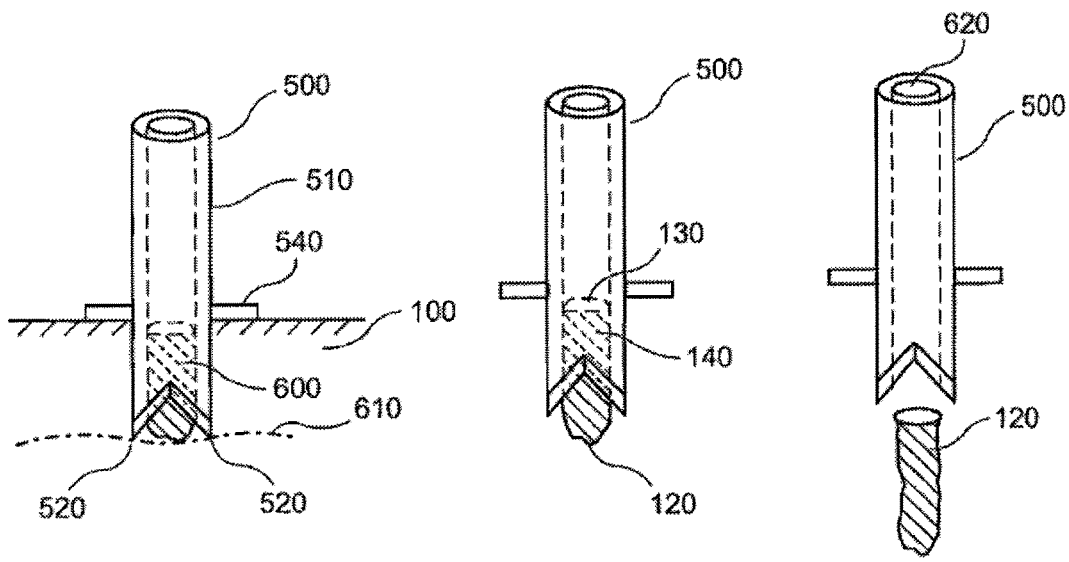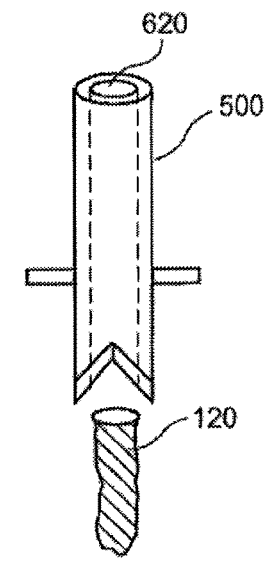
FIG. 6A  FIG. 6B  FIG. 6C

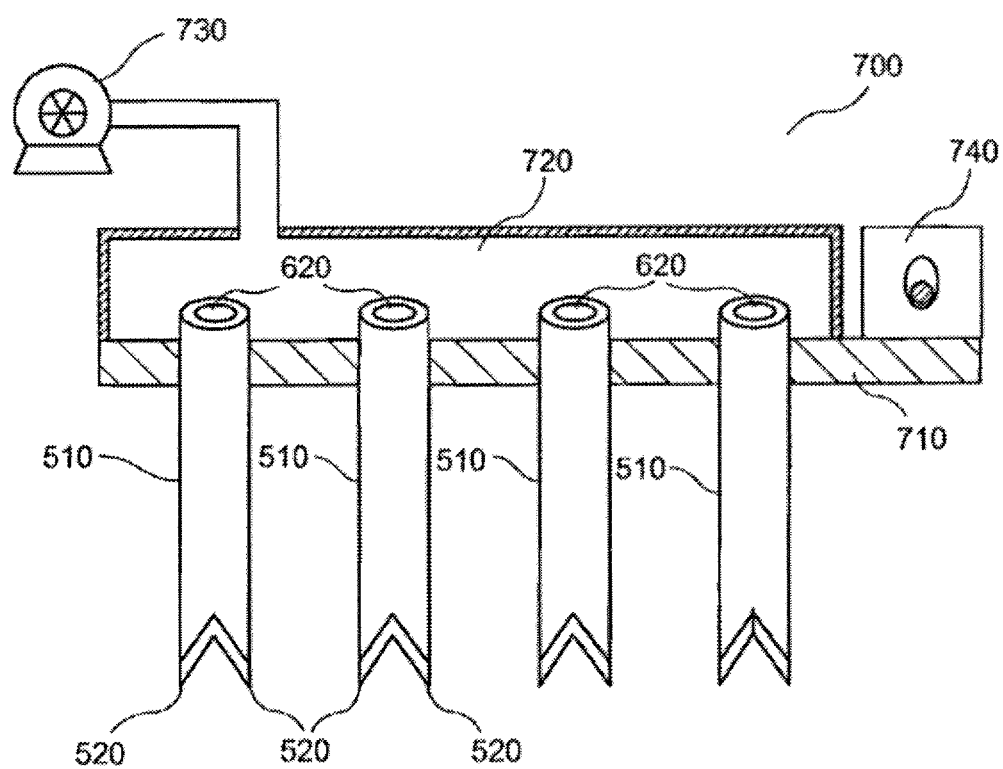
F I G. 7

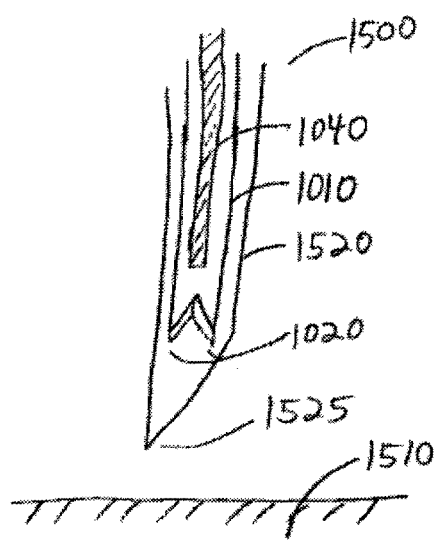 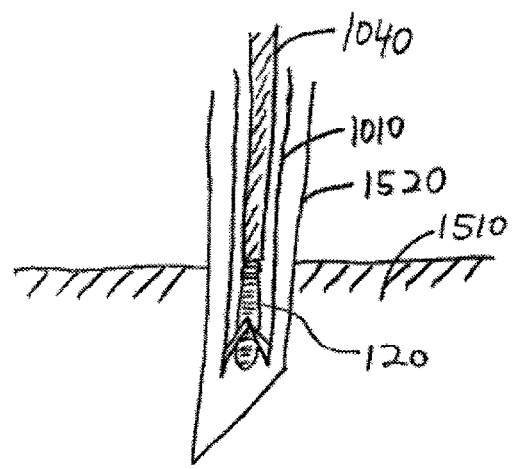
FIG. 15A  FIG. 15B
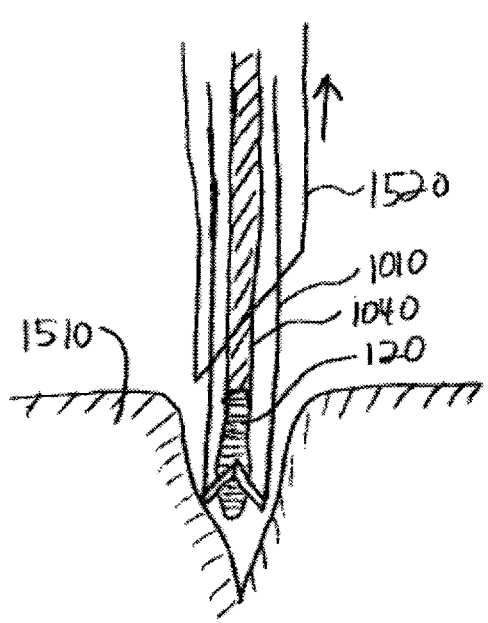 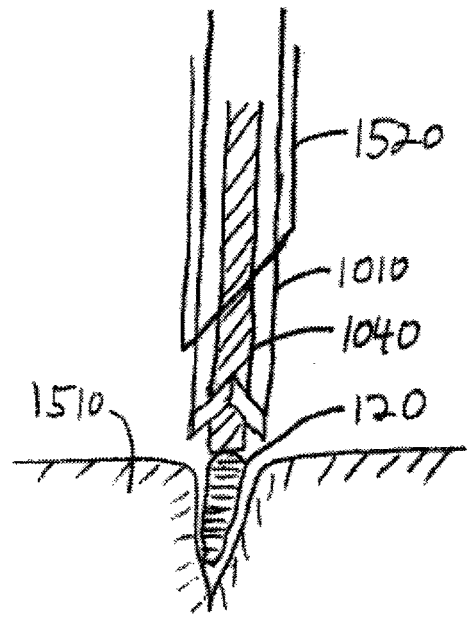
FIG. 15C  FIG. 15D

METHOD AND APPARATUS FOR TISSUE GRAFTING AND COPYING

CROSS-REFERENCE TO RELATED APPLICATIONS

This is a divisional application of U.S. patent application Ser. No. 13/102,711 filed May 6, 2011, which claims benefit to U.S. Provisional Patent Applications 61/332,230 filed May 7, 2010, 61/373,498 filed Aug. 13, 2010 and 61/437,507 filed Jan. 28, 2011.

FIELD OF THE DISCLOSURE

The present disclosure relates to exemplary embodiments of method and apparatus for providing tissue grafts and reproducing tissue structures using tissue, e.g., from a donor site.

BACKGROUND INFORMATION

An autograft can refer to tissue transplanted from one part of an individual's body (e.g., a "donor site") to another part (e.g., a "recipient site"). Autografts can be used, for example, to replace missing skin and other tissue and/or to accelerate healing resulting from trauma, wounds, burns, surgery and birth defects. Availability of tissue for autografting can be limited by characteristics of candidate donor sites, including a number and/or total area of tissue grafts, healing behavior of the donor site, similarity of the donor and recipient sites, aesthetic considerations, etc.

Skin grafting can be performed surgically. For example, a conventional autograft procedure may include excision or surgical removal of burn injured tissue, choosing a donor site, which may be an area from which healthy skin is removed to be used as cover for the cleaned burned area, and harvesting, where the graft may be removed from the donor site, e.g., using an instrument similar to an electric shaver. Such instrument (e.g., a dermatome) can be structured to gently shave a piece of tissue, which may be, e.g., about $10/1000$ of an inch thick for a split-thickness graft, from the skin at the unburned donor site to use as a skin graft. The skin graft can then be placed over the cleaned wound so that it can heal. Donor skin tissue can be removed to such a depth that the donor site can heal on its own, in a process similar to that of healing of a second degree burn.

Two conventional types of autografts which may be used for a permanent wound coverage include sheet grafts and meshed grafts. A sheet graft can refer to a piece of skin tissue removed from an undamaged donor site of the body, in a process that may be referred to as harvesting. The size of the donor skin piece that is used may be about the same size as the damaged area. The sheet graft can be applied over the excised wound, and stapled or otherwise fastened in place. The donor skin tissue used in sheet grafts may not stretch significantly, and a sheet graft can be obtained that is slightly larger than the damaged area to be covered because there may often be a slight shrinkage of the graft tissue after harvesting.

Sheet grafts can provide an improved appearance of the repaired tissue site. For example, sheet grafts may be used on large areas of the face, neck and hands if they are damaged, so that these more visible parts of the body can appear less scarred after healing. A sheet graft may be used to cover an entire burned or damaged region of skin, e.g., if the damaged site is small. Small areas of a sheet graft can be lost after placement because of a buildup of fluid (e.g., a hematoma) can occur under the sheet graft following placement the sheet graft.

Sheet grafts may be full-thickness or split-thickness. For example, split-thickness skin grafts can be used to cover wounds in burn and skin ulcer patients. A conventional split-thickness graft can be formed, e.g., by harvesting a sheet of epidermis and upper dermal tissue from a donor site, in a procedure similar to that of peeling an apple. The split-thickness graft can then be placed on the location of the burn or ulcer. The skin tissue may then grow back at the donor site following a generally extended healing time. Split-thickness grafts may be preferable to full-thickness grafts because removing large amounts of full-thickness skin tissue from the donor site can lead to scarring and extensive healing times at the donor site, as well as an increased risk of infection. However, skin tissue removed from the donor site for a split-thickness skin autograft can include only a thin epithelial layer, which can lack certain elements of the dermis that improve structural stability and normal appearance in the recipient site.

Full-thickness skin grafts can be formed using sheets of tissue that include the entire epidermis layer and a dermal component of variable thickness. Because the dermal component can be preserved in full-thickness grafts, more of the characteristics of normal skin can be maintained following the grafting procedure. Full-thickness grafts can contain a greater collagen content, dermal vascular plexus, and epithelial appendages as compared to split-thickness grafts. However, full-thickness grafts can require more precise conditions for survival because of the greater amount of tissue requiring revascularization.

Full-thickness skin grafts can be preferable for repairing, e.g., visible areas of the face that may be inaccessible by local flaps, or for graft procedures where local flaps are contraindicated. Such full-thickness skin grafts can retain more of the characteristics of normal skin including, e.g., color, texture, and thickness, as compared to split-thickness grafts. Full-thickness grafts may also undergo less contraction while healing. These properties can be important on more visible areas such as the face and hands. Additionally, full-thickness grafts in children can be more likely to grow with the individual. However, the application of conventional full-thickness skin grafts can be limited to relatively small, uncontaminated, well-vascularized wounds, and thus may not be appropriate for as many types of graft procedures as split-thickness grafts. Additionally, donor sites for full-thickness grafts can require surgical closure or resurfacing with a split-thickness graft.

A meshed skin graft can be used to cover larger areas of open wounds that may be difficult to cover using sheet grafts because of, e.g., a lack of a sufficient area of healthy donor sites. Meshing of a skin graft can facilitate skin tissue from a donor site to be expanded to cover a larger area. It also can facilitate draining of blood and body fluids from under the skin grafts when they are placed on a wound, which may help prevent graft loss. The expansion ratio (e.g., a ratio of the unstretched graft area to the stretched graft area) of a meshed graft may typically be between about 1:1 to 1:4. For example, donor skin can be meshed at a ratio of about 1:1 or 1:2 ratio, whereas larger expansion ratios may lead to a more fragile graft, scarring of the meshed graft as it heals, and/or extended healing times.

A conventional graft meshing procedure can include running the donor skin tissue through a machine that cuts slits through the tissue, which can facilitate the expansion in a pattern similar to that of fish netting or a chain-link fence.

Healing can occur as the spaces between the mesh of the stretched graft, which may be referred to as gaps or interstices, fill in with new epithelial skin growth. However, meshed grafts may be less durable graft than sheet grafts, and a large mesh can lead to permanent scarring after the graft heals.

To help the graft heal and become secure, the area of the graft can preferably be made immobile (e.g., not moved) for at least about five days following each surgery. During this immobilization period, blood vessels can grow from underlying tissue into the skin graft, and can help to bond the two tissue layers together. About five days after the graft is placed, exercise therapy programs, tub baths, and other normal daily activities can often be resumed. Deep second-degree and full-thickness burns may require skin graft surgery for quick healing and minimal scarring. Large burn sizes can lead to more than one grafting procedure during a hospital stay, and may require long periods of immobilization for healing.

As an alternative to autografting, skin tissue obtained from recently-deceased people (which may be referred to, e.g. as a homograft, an allograft, or cadaver skin) can be used as a temporary cover for a wound area that has been cleaned. Unmeshed cadaver skin can be put over the excised wound and stapled in place. Post-operatively, the cadaver skin may be covered with a dressing. Wound coverage using cadaveric allograft can then be removed prior to permanent autografting.

A xenograft or heterograft can refer to skin taken from one of a variety of animals, for example, a pig. Heterograft skin tissue can also be used for temporary coverage of an excised wound prior to placement of a more permanent autograft, and may be used because of a limited availability and/or high expense of human skin tissue. In some cases religious, financial, or cultural objections to the use of human cadaver skin may also be factors leading to use of a heterograft. Wound coverage using a xenograft or an allograft is generally a temporary procedure which may be used until harvesting and placement of an autograft is feasible.

Epithelial appendages can be regenerated following a grafting procedure. For example, hair can be more likely to grow from full-thickness grafts than from split-thickness grafts, but such hair growth may be undesirable based on the location of the wound. Accordingly, donor sites for full-thickness grafts can be carefully selected based in part, e.g., on patterns of hair growth at the time of surgery. Further, certain hair follicles may not be oriented perpendicular to the skin surface, and they can be transected if an incision provided to remove graft tissue is not oriented properly.

Sweat glands and sebaceous glands located in graft tissue may initially degenerate following grafting. These structures can be more likely to regenerate in full-thickness grafts than in split-thickness grafts because full-thickness grafts can be transferred as entire functional units. For example, sweat gland regeneration can depend in part on reinnervation of the skin graft with recipient bed sympathetic nerve fibers. Once such ingrowth has occurred, the skin graft can assume the sweating characteristics of the recipient site, rather than retaining the characteristics of the donor site. In contrast, sebaceous gland regeneration may be independent of graft reinnervation and can retain the characteristics of the donor site. Prior to the regeneration, the skin graft tissue may lack normal lubrication of sebum produced by these glands, which can make such grafts more susceptible to injury.

In general, grafting procedures may be limited by the amount of tissue which can be removed from the donor site without causing excessive adverse effects. Full-thickness grafts can provide improved tissue quality at the wound site, but the donor site may be more severely disfigured as described above. Split-thickness grafts can be a compromise between healing times and aesthetic and functional properties of the donor and recipient sites, whereas meshing can provide more extensive graft coverage at the expense of visible scarring.

Harvesting of the graft tissue from the donor site can generally generate undesirable large-scale tissue damage to the donor site. On the other hand, small areas of skin wounding adjacent to healthy tissue can be well-tolerated, and may heal quickly. Such healing of small wounds can occur in techniques such as "fractional photothermolysis" or "fractional resurfacing," in which patterns of damage having a small dimension can be created in skin tissue. These exemplary techniques are described, e.g., in U.S. Pat. No. 6,997,923 and U.S. Patent Publication No. 2006/0155266. Small-scale damage patterns can heal quickly by regrowth of healthy tissue, and can further provide desirable effects such as skin tightening without visible scarring.

In view of the shortcomings of the above described procedures for tissue grafting, it may be desirable to provide exemplary embodiments of method and apparatus that can provide tissue suitable for grafting, e.g., while minimizing unwanted damage to the donor sites.

SUMMARY OF EXEMPLARY EMBODIMENTS

Exemplary embodiments of the present disclosure provide method and apparatus for obtaining small portions of graft tissue that can be accompanied by rapid healing of the donor site. For example, the exemplary embodiment of the method can be provided for obtaining skin graft tissue by harvesting small portions of the tissue, e.g., micrografts, from a donor site. Such micrografts can be used to form grafts or "copy" tissue to generate larger tissue structures from the small tissue samples.

Such micrografts can comprise skin tissue that can include, e.g., epidermal and dermal tissue, and/or tissue obtained from other body organs. The micrografts can have at least one dimension that is relatively small, e.g., less than about 1 mm, or less than about 0.5 mm, or optionally about 0.3 mm or less, or about 0.2 mm. Such exemplary small dimensions of the micrografts can facilitate both healing of the donor site following harvesting and viability of the micrografts by allowing greater diffusional nourishment of the micrograft tissue. The small regions of damage in the donor site caused by a removal of the tissue portions can heal rapidly with little or no formation of visible scars. The micrografts obtained from skin tissue can include, e.g., epidermal and dermal tissue, and can also include stem cells that can be located proximal to the dermal/fatty layer boundary. The micrografts can also be obtained from other types of tissue, e.g., various internal organs or the like.

A fraction of dermal tissue that is removed from a donor site can be, e.g., less than about 70%, or less than about 50%, although other fractions may be used. The harvested tissue portions can be in the shape of cylinders, elongated strips, or other geometries which can include at least one small dimension. In certain exemplary embodiments, a portion of the tissue at the donor site may be frozen or partially frozen. Such freezing may facilitate cutting, removal and/or viability of the harvested tissue portions.

In a further exemplary embodiment of the present disclosure, an apparatus for harvesting micrografts can be provided that includes at least one hollow tube with a pin provided at least partially within the tube, wherein the pin is controllably translatable in a direction along the longitudinal axis of the tube. The diameter of the pin can be substantially the same as the internal diameter of the lumen of the tube, or it can be slightly smaller.

Such tube(s) and corresponding pin(s) can be mechanically coupled to a substrate having at least one hole therethrough. A plurality of linear actuators can be provided to controllably position and/or move the at least one tube and pin relative to the substrate. For example, the actuators can be configured to position the at least one tube through a hole in the substrate and control a distance that the distal end of the tube protrudes from a lower surface of the substrate. The actuators can further be configured to independently control the position of the pin within the tube. The substrate can be configured to be positioned on the surface of a tissue to facilitate harvesting of micrografts from the tissue and/or implantation of micrografts into the tissue.

In further exemplary embodiments of the present disclosure, a plurality of tubes and corresponding pins can be provided to facilitate harvesting of a plurality of micrografts. A plurality of actuators or mechanical arrangements can be provided in communication with the proximal ends of the tubes and/or pins to facilitate precise positioning and translation of the plurality of tubes and pins relative to each other and to the tissue. The actuators can be configured to translate all of the tubes and/or pins simultaneously, or optionally to translate certain ones of the tubes or pins independently of the other tubes. A vibrating arrangement can be coupled to the apparatus to facilitate the insertion of the tubes into the donor and/or recipient site.

The exemplary micrografts can be placed in a biocompatible matrix, e.g., to form a graft or larger copy of the donor tissue, or may be implanted directly into tissue at the recipient site. The biocompatible matrix can be formed using collagen, polylactic acid, hyaluronic acid, and/or other substances which can support the harvested micrograft tissue portions and promote their growth. The matrix can optionally include, e.g., nutrients, growth factors, and/or other substances to promote tissue growth or viability. The harvested tissue portions can be bonded to the matrix using techniques such as photochemical tissue bonding to provide structural stability. The matrix can then be applied to the recipient site, which can promote growth and revascularization of the tissue portions to form a continuous sheet of the grafted tissue. Optionally, the matrix can be placed in a suitable environment to facilitate growth of the micrografts therein, which can then form a larger portion of tissue 'copied' from the donor site.

The exemplary micrografts can also be gathered in a compact configuration to form graft tissue that can be applied directly to a recipient site. The exemplary micrografts can also be inserted directly into the tissue at a recipient site such as, e.g., scar tissue, using, e.g., the exemplary hollow tubes described herein. In certain exemplary embodiments, the micrografts can be harvested from a donor site tissue that is different from the tissue type at the recipient site to form various types of heterografts.

Still further exemplary embodiments of the present disclosure can provide methods for extracting or harvesting micrografts from a tissue and optionally place them directly in a matrix material. For example, such exemplary methods can utilize an exemplary apparatus that includes at least one tube and pin provided therein to harvest tissue as follows:

A) A portion or sheet of a matrix material can be placed on a donor tissue site, and the distal ends of the tube and pin provided within the tube can each be positioned proximal to the upper surface of the matrix.

B) The tube and pin can be translated together to penetrate through the matrix and be positioned proximal to the surface of the donor site.

C) The tube can then be translated downward into the tissue of the donor site to sever a portion of the tissue from the surrounding tissue, while the distal end of the pin remains at the surface of the donor site.

D) The tube and pin can then be retracted simultaneously until the distal end of the tube is proximal to the lower surface of the matrix material or within the matrix material, and a micrograft comprising the severed tissue remains within the distal portion of the tube.

E) The tube can then be further retracted from the matrix while the pin location is held substantially stationary relative to the matrix, such that the micrograft is held within the matrix material by the stationary pin and remains within the matrix as the tube is retracted from around the micrograft.

In yet another exemplary embodiment of the present disclosure, a piercing needle can be provided around at least a portion of the hollow tube and pin. The apparatus including at least one hollow tube, pin, and piercing needle can be configured to place a micrograft contained within a distal portion of the hollow tube into tissue located at a recipient site. The piercing needle can be inserted into tissue at a recipient site. The hollow tube containing the pin and a harvested micrograft in the distal portion thereof can be advanced through the piercing tube such that the distal end of the hollow tube is proximal to or below the surface of the recipient site. The piercing needle can be withdrawn from the recipient site, while the hollow tube is held stationary. The hollow tube can then be withdrawn while holding the pin within the tube stationary relative to the recipient site. In this manner, the micrograft can remain within the tissue of the recipient site, e.g., held there by the pin as the hollow tube is withdrawn. The pin can subsequently be withdrawn to leave the micrograft within the recipient site where the tissue was initially separated by the piercing needle. A substrate can be provided with at least one opening therethrough and configured to be placed on the tissue surface, to facilitate positioning of the needle, tube and/or pin relative to the tissue being treated and/or to facilitate mechanical stabilization of the tissue during treatment.

These and other objects, features and advantages of the present disclosure will become apparent upon reading the following detailed description of exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which:

FIG. 3A is a schematic illustration of another exemplary donor site after elongated strips of tissue have been harvested therefrom;

FIG. 3B is a schematic illustration of the exemplary donor site shown in FIG. 3A after healing has occurred;

FIG. 3C is a schematic illustration of an exemplary tissue strip that may be removed from the donor site shown in FIG. 3A;

FIG. 4A is a schematic view in plan of a plurality of exemplary cylindrical micrograft tissue portions provided in a compact arrangement to form a graft;

FIG. 4B is a side view of the exemplary micrograft tissue portions shown in FIG. 4A;

FIG. 5A is a schematic illustration of an exemplary apparatus that can be used to harvest micrograft tissue in accordance with further exemplary embodiments of the present disclosure;

FIG. 5B is a schematic illustration of the exemplary apparatus that can be used to harvest the micrograft tissue in accordance with further exemplary embodiments of the present disclosure;

FIG. 6A is a schematic illustration of the exemplary apparatus shown in FIG. 5A that is inserted into an exemplary donor site to harvest an exemplary micrograft;

FIG. 6B is a schematic illustration of the exemplary apparatus shown in FIG. 5A that contains the harvested micrograft;

FIG. 6C is a schematic illustration of the exemplary apparatus shown in FIG. 5A showing the harvested micrograft being removed therefrom;

FIG. 7 is a schematic illustration of the exemplary apparatus that can be used to harvest micrograft tissue in accordance with further exemplary embodiments of the present disclosure;

FIGS. 15A-15E are schematic illustrations of an exemplary apparatus and procedure for placing harvested micrographs directly into tissue at a recipient site;

Figure 1A:
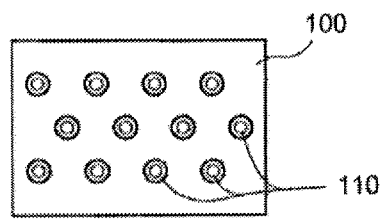
FIG. 1A is a schematic illustration of an exemplary donor site after cylindrical portions of micrograft tissue have been harvested therefrom.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

According to exemplary embodiments of the present disclosure, methods and apparatus can be provided for producing autografts, and particularly such methods and apparatus which can facilitate more rapid healing of the donor site while providing improved tissue characteristics at the recipient site. Exemplary embodiments of the present disclosure can include a plurality of small-scale tissue portions (e.g., micrografts) that can be used to provide autografts. Such micrografts can avoid significant permanent damage to the donor site while providing graft tissue that can heal rapidly and generate skin tissue having desirable properties at the recipient site.

In exemplary embodiments of the present disclosure, a method can be provided for creating autografts in which tissue portions having at least one small dimension (e.g., micrografts) are harvested from an exemplary donor site 100, as shown in FIG. 1A. The holes 110 shown in FIG. 1A represent regions of the exemplary donor site 100 from which tissue portions (e.g., micrografts) have been removed.

These exemplary holes 110 can have an approximately round cross-sectional shape, although other shapes may be used.

Figure 1B:
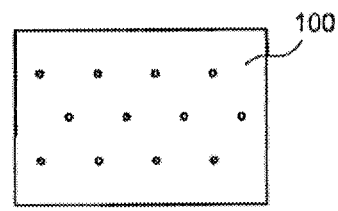
FIG. 1B is a schematic illustration of the exemplary donor site shown in FIG. 1A after healing has occurred.

The exemplary donor site 100 is shown in FIG. 1B after healing of the harvested tissue has occurred. The small regions of damage 100 created at the donor site by the removed tissue can heal rapidly and/or without visible scarring. For example, the residual pattern of the healed donor site 100 shown in FIG. 1B may not be easily perceptible by the naked eye under normal viewing conditions.

Figure 1C:
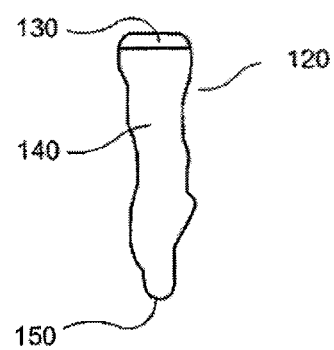
FIG. 1C is a schematic illustration of an exemplary micrograft that can be removed from the exemplary donor site shown in FIG. 1A.

An exemplary micrograft 120 that can be formed, e.g., by harvesting or removing a portion of the tissue from the donor site 100 to form the hole 110 therein, is shown in FIG. 1C. The exemplary micrograft 120 can have an elongated shape that may be approximately cylindrical. The micrografts 120 can include both epidermal tissue 130 and dermal tissue 140 from the exemplary donor site 100. For example, the exemplary micrograft 120 can be about 3 mm in length, which can correspond to a typical total depth of the skin layer (e.g., epidermal and dermal layers). A different length may be used based on the particular skin or tissue characteristics of the donor site 100. In general, it can be preferable to avoid harvesting a significant amount of subcutaneous tissue, so the harvested micrografts 200 can include primarily the epidermal tissue 130 and the dermal tissue 140. A lower portion 150 of the exemplary micrograft 120 can also include stem cells that can be present in a lower portion of the dermal layer of the donor site 100 (e.g., near a dermal/fatty layer boundary).

A width or diameter of the holes 110 produced during harvesting (which can correspond approximately to the diameters of the portions of the harvested micrografts 120) can be less than about 2 mm, or less than about 1 mm. In certain exemplary embodiments of the present disclosure, the diameter or width of a micrograft 120 can be less than about 0.5 mm, less than about 0.3 mm, or about 0.2 mm. The size of the exemplary holes 110 can be selected, e.g., based on the effects of creating small damage regions in the donor site 100 that can heal rapidly and/or without scarring, and on creating portions of tissue that can be small enough to promote viability when transplanted or placed in a growth medium, and large enough to form a sufficient amount of graft tissue and/or capture tissue structures that may be present in the donor tissue.

For example, living tissue can be provided with nutrients via a diffusional transport over distances of about 0.1 mm. Accordingly, the exemplary micrografts 120 having at least one dimension that is less than about 0.5 mm, e.g., less than about 0.3 mm or, e.g., as small as about 0.2 mm, can exhibit improved viability and likelihood to survive, and they may grow when used in a graft. Such exemplary micrografts 120 can be better able to receive nutrients (including, e.g., oxygen) when placed in a recipient site, prior to revascularization of the tissue.

Larger micrografts 120, e.g., those having a width of about 1-2 mm, can also benefit from such diffusional transport of nutrients, and can also be more likely to survive than significantly larger portions of graft tissue (e.g., conventional full-thickness, split-thickness or meshed grafts). These larger sizes can be preferable for harvested tissue that is heterogeneous, e.g., tissues that may contain certain structures that can be preserved within a single micrograft 120. For example, skin tissue has certain structures such as hair follicles, sebaceous glands, etc., and harvesting somewhat larger micrografts 120 from skin may help to preserve these tissue structures when harvested and transplanted. On the other hand, smaller micrografts, e.g. those less than about 0.5 mm, or about 0.2 mm wide, can be suitable for relatively homogeneous tissues, such as muscle tissue, where there are few or no larger structures in the tissue to be preserved.

A fraction of surface tissue removed from the donor site 100 by harvesting (which can correspond to a fractional surface area of the exemplary donor site 100 occupied by the holes 110) can be less than about 70%, or more preferably less than about 50%. The fraction of tissue removed can be sufficiently large to provide enough harvested micrografts 120 to form a graft therefrom of appropriate size, but small enough to facilitate rapid healing at the donor site 100 based on growth from the remaining undamaged tissue. Other fractions of tissue can be removed from a donor site 100 depending on factors such as, e.g., the particular characteristics of the donor site 100, the size of the graft needed, and the overall amount of donor site tissue available.

Figure 2A:
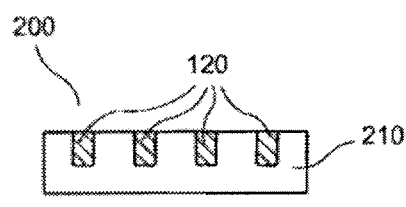
FIG. 2A is a cross-sectional view of an exemplary graft prepared by providing harvested micrograft tissue portions in a biocompatible matrix.
Figure 2B:
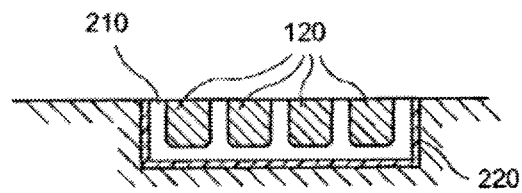
FIG. 2B is a is a cross-sectional view of the exemplary graft shown in FIG. 2A after it has been placed over a wound and some regrowth has occurred.

In further exemplary embodiments of the present disclosure, a graft 200 can be provided by embedding or inserting a plurality of micrografts 120 in a biocompatible matrix 210 as shown, e.g., in FIG. 2A. The exemplary matrix 210 containing the micrografts 120 can be exposed to nutrients to promote growth of the harvested micrografts 120, e.g., to form a continuous or nearly continuous layer of tissue in the graft 200 after growth has occurred. The exemplary graft 200, which can include the matrix 210 and the micrografts 120, may be placed directly over a recipient site 220 (e.g., a cleaned wound area) as shown in FIG. 2B. The exemplary micrografts 120 can also include stem cells as described herein, which can also facilitate healing and integration of the exemplary micrografts 120 when they are transplanted to the recipient site 220. The recipient site 220 can provide nutrients and/or promote revascularization of the harvested micrografts 120, which can further enhance their growth through the matrix 210 to eventually fill in the spaces separating them. For example, FIG. 2B shows the micrografts 120 after they have begun to grow into the surrounding matrix 210.

In one exemplary embodiment of the present disclosure, the micrografts 120 can be placed in the matrix 210 at approximately the same spacing (e.g., a similar areal density) as they were removed from the donor site 100. This exemplary configuration can generate an amount of graft tissue that may be approximately the same size as the overall harvested area of the donor site 100 after the micrografts 120 grow and fill in the spaces between them with new tissue. The average spacing of the micrografts 120 in the matrix 210 can also be increased to form a graft tissue that is larger than the overall area of the harvested donor site 100. The particular spacing of the micrografts 120 in a particular graft 200 can be selected based on factors such as, e.g., the size and fractional damage of the donor site 100, the size of the recipient site 220 to be covered by the skin graft 200, the time needed for the micrografts 120 to regrow and form a continuous tissue layer, the desired appearance of the grafted recipient site, etc. For example, the exemplary micrografts 120 can be spaced far apart in a particular graft, which can provide a larger graft area but can also require longer healing time and the possibility of some visible scarring or texture in the healed graft 200.

In a further exemplary embodiment of the present disclosure, tissue portions 320, such as those shown in FIG. 3C, can be harvested in an elongated, narrow strip-like shape. One or more of the exemplary tissue strips 320 can include both epidermal tissue 130 as well as dermal tissue 140, which can be similar to the micrograft 120 shown in FIG. 1C. For example, the height of the exemplary tissue strip 320 can be about 3 mm, or another length that may correspond to a local depth of the dermal layer at the donor site 100. Larger and/or smaller depths of the dermal layer can also be selected when harvesting tissue strips 320 based on, e.g., characteristics of the donor and recipient sites, the wound to be repaired by grafting, etc.

Harvesting of such exemplary tissue strips 320 can leave long, narrow grooves 310 in a donor region 100 as shown, e.g., in FIG. 3A. A width of the grooves 310 (and thus a width of the harvested tissue strips 320) can be less than about 1 mm, or less than about 0.5 mm. In certain exemplary embodiments, the width of such tissue strips can be less than about 0.3 mm, or about 0.2 mm. As described herein, such a small dimension can facilitate diffusional transport of nutrients to the graft tissue and can improve viability of the harvested tissue. A depth of the grooves 310 from the skin surface can correspond to the height of the harvested strips 320.

A surface area fraction of the exemplary donor site 310 that is removed to form tissue strips 320 can be less than about 70%, or about 50% or less. Factors governing a selection of parameters associated with the harvested elongated tissue strips 320 (e.g., widths and area fractions removed from the donor site) may be similar to those described above with respect to the substantially cylindrical micrografts 120. The length of the harvested strips 320 can be selected based on factors such as, for example, ease of cutting, removing, and handling the thin tissue strips 320, the size of the donor site 100, etc. The elongated grooves 310 formed in the donor site may also be able to heal rapidly with little or no visible scarring, as shown in FIG. 3B, because of the small lateral dimension and presence of adjacent healthy tissue that can support local tissue regrowth.

The harvested strips 320 can be placed, e.g., in a biocompatible matrix similar to the matrix 210 shown in FIG. 2A. The tissue strips 320 can be arranged in an approximately parallel configuration, e.g., corresponding to the configuration of the donor-site grooves 310 from which they were removed. The spacing between the strips 320 can alternatively be increased or decreased relative to the spacing of the grooves 310 in the donor site 100 as desired, e.g., to provide either larger overall areas of graft tissue or more densely packed graft tissue, respectively. Such harvested tissue strips 320 can be used for certain grafting procedures because the long dimension can preserve structures in the harvested skin tissue that may promote revascularization and improve healing of the graft formed therefrom.

Harvested tissue portions can be removed from the donor site in other shapes, including tile patterns or fractal-like shapes. In general, each removed piece of tissue (and, e.g., each corresponding hole or void in the donor site) can have at least one small dimension that is less than about 1 mm, or less than 0.5 mm. In certain exemplary embodiments, this small dimension can be less than about 0.3 mm, or about 0.2 mm.

In further exemplary embodiments of the present disclosure, the harvested tissue portions can be placed at the recipient site in a dense configuration. For example, FIG. 4A shows a schematic top view of a plurality of substantially cylindrical micrografts 120 that can be gathered in an exemplary dense arrangement, e.g., where adjacent ones of the exemplary micrografts 120 are in at least partially direct contact each other. FIG. 4B is a schematic side view of the micrografts 120 shown in FIG. 4A. This exemplary dense configuration can provide a graft that is smaller than the overall area of the harvested donor site 100, but which can tend to heal faster and be less likely to produce visible scarring than grafts formed using spaced-apart harvested tissue portions 120, 320. Similar exemplary dense configurations of the harvested tissue can be formed using, e.g., elongated strips of tissue 320 shown in FIG. 3C or the like.

The exemplary biocompatible matrix 210 can be formed using one or more materials structured to provide mechanical stability and/or support to the harvested micrografts 200, and/or which may promote tissue regrowth. Examples of materials which can be used to form the matrix 210 can include polylactic acid (PLA), collagen (e.g., a collagen sponge), low melting agarose (LMA), hyaluronic acid (e.g., hyaluronan), or devitalized animal or cadaveric skin. The matrix 210 can, for example, be formed of allogeneic skin that can be prepared, e.g., by freezing and thawing a portion of donor skin tissue several times. For example, about seven freezing/thawing cycles can be performed to effectively kill the cells in the donor skin for use as a matrix 210. The frozen and thawed tissue can then be washed with a detergent or other composition to remove dead cells, debris, etc.

In a further exemplary embodiment of the present disclosure, living donor skin tissue samples can be treated with radiation to form the matrix material 210. For example, donor skin tissue can be treated with lethal doses of x-rays, e.g. gamma rays, which can leave the cells intact. Cells in the donor matrix material may thus stay alive for a particular duration after radiation exposure, e.g., about 48-72 hours, before dying. Such a matrix 210 including short-lived cells can initially support growth of implanted micrografts 120 but then die off before any significant interactions adverse to growth and/or viability of the micrografts 120 can occur such as, e.g., autoimmune responses. Alternatively, the implantation of such an irradiated matrix 210 with the viable micrografts 120 can be delayed for a sufficient time after irradiation, e.g., about 72 hours or more, to avoid any autoimmune response between the micrografts 120 and the matrix 210. The matrix 210 can also be prepared from donor skin, for example, by washing the cells away with detergent and acidic/basic solutions. An exemplary protocol for preparing such matrices or scaffolds is described, e.g., in Alsberg et al., Proc Natl Acad Sci USA. 2002 Sep. 17; 99(19): 12025-12030.

In a further exemplary embodiment of the present disclosure, small portions of a matrix material as described herein can be combined with the micrografts 120, e.g., in a configuration similar to that shown in FIGS. 4A and 4B, except that some of the columns are formed of matrix material. The micrografts 120 and matrix columns can be adhered using, e.g., adhesives, photochemical bonding, etc. The relative sizes and numbers of the micrografts 120 and portions of matrix material can be varied to generate a compound substance that has a particular fraction of micrograft material.

Nutrients or other additives can also be provided in the matrix 210 to further promote tissue regrowth. Such additives can include, e.g., one or more growth factors, stem cells, etc. Examples of such growth factors include, but are not limited to, vascular endothelial growth factor (VEGF), platelet-derived growth factor (PDGF), transforming growth factor beta (TGF-β), and fibroblast growth factor (FGF), which may enhance or promote vascularization of the grafts. Epidermal growth factor (EGF) and keratinocyte growth factors can also be used, and may increase mobilization and differentiation of certain skin cells, such as keratinocytes and fibroblasts. Platelet-rich plasma (which can be prepared, e.g., from a patient's own blood, using commercially available systems) can also be used to provide certain growth factors. Although such plasma can be more labor-intensive to prepare (from the standpoint of clinical personnel) than exogenous growth factors, it may provide a better approximation of the natural wound-healing environment. Such growth factors can be introduced to the matrix 210, e.g. a LMA/collagen mix, at a moderate temperature where the matrix is still in a liquid form. The LMA/collagen matrix can then be formed by adjusting the pH value of the collagen solution before combining it with heated LMA. For a solidification of the matrix 210, for example, the mix can be stored for about 20 min at a temperature of about 37° C. before cooled it down to about 4° C.

Stem cell sources can include, e.g., adipose tissue-derived stem cells and/or bone marrow-derived mesenchymal stem cells. Micrografts obtained or harvested from skin tissue may also contain stem cells from hair follicles. Such stem cells or other cells can be incorporated into the matrix by culturing the cells with the matrix prior to implantation of micrografts. Low-level light therapy (LLLT) can also be used to facilitate growth and viability of the micrografts. For example, red or near-infrared light can be used to illuminate the donor site and/or the recipient site after tissue harvesting and placement of the graft tissue to further promote healing and/or growth of the tissue.

Growth factors and/or other additives may be introduced into the matrix, e.g., by soaking the matrix material in a solution containing growth factors prior to implantation of micrografts therein. The growth factors can also be introduced by releasing them into the matrix over time using a controlled-release mechanism, e.g., by directing or pumping the growth factors from a reservoir into the matrix over time, or by embedding growth factors in a biodegradable polymer that can be introduced into the matrix. Certain growth factors or additives can also be attached to the matrix material by chemical bonds that can be severed over time, thereby releasing the growth factors into the matrix gradually.

In certain exemplary embodiments of the present disclosure, certain techniques such as photochemical tissue bonding can be used to improve mechanical stability of the micrografts 120 and/or tissue strips 320 in the matrix 210. For example, a technique for a photochemical tissue bonding is described in U.S. Pat. No. 7,073,510. This technique includes an application of a photosensitizer to a tissue, followed by irradiation with electromagnetic energy to produce a tissue seal. For example, a photosensitizer such as Rose Bengal can be applied to the matrix 210 containing the exemplary micrografts 120 and/or tissue strips 320, followed by exposure of the matrix to green light for about two minutes. Photochemical tissue bonding can catalyze a polymerization reaction which may facilitate a stronger bonding of the micrografts 120 and/or tissue strips 320 to the matrix 210, where the matrix 210 can include a protein such as, e.g., hyaluronic acid or collagen.

In further exemplary embodiments of the present disclosure, the matrix material can be provided in a liquid or gel precursor form that can be mixed with the micrografts 120. The matrix material can then be solidified or gelled (e.g., either before or after introducing the mixture of micrografts 120 and matrix material into the recipient site). Solidification of the matrix material to form the matrix 210 can be achieved using various procedures based on the matrix material used. For example, collagen gels (such as those depicted in FIG. 16) can be provided in liquid form at lower temperatures, and may be solidified by raising the temperature to about 37° C. Other matrices 210 can be formed using polymers that can be solidified by chemical cross-linking mechanisms. Such mechanisms can be activated, catalyzed and/or initiated, e.g., by temperature, light (similar to photochemical tissue bonding), a change in pH, or the like.

If the micrografts 120 are provided in the matrix 210 that is initially in a liquid form, the orientation of the micrografts 120 within the matrix 210 can be set and/or maintained in several ways. For example, a lipid-rich material can be applied to the an upper end or portion of the micrograft 120 (e.g., the epidermal surface of the micrograft 120 obtained from skin tissue), such that the tops of the micrografts 120 would tend to float to the surface of the liquid matrix material, thereby aligning the upper ends of the micrografts 120 towards the upper surface of the matrix 210. Alternatively, a metallic paint can be applied to an upper portion of the micrografts 120, and a magnetic field can then be applied proximal to the graft material to align the micrografts 120 within the matrix material. Such exemplary alignment procedures can be performed before and/or during solidification or gelation of the matrix material to produce a matrix 210 that has micrografts 120 therein that have a particular orientation. Alternatively, in certain exemplary embodiments of the present disclosure, the micrografts 120 can be provide in the matrix 210 without a particular preferred orientation.

In still further exemplary embodiments of the present disclosure, an apparatus 500 can be provided, such as that shown in FIG. 5A, which can facilitate harvesting of the exemplary micrografts 120 from the donor site 100 as described herein. The exemplary apparatus 500 can include a hollow tube 510 that can be formed of metal or another structurally rigid material. For example, the tube 510 can be formed using a stainless steel tube, a biopsy needle, or a similar structure. The tube 510 can be coated with a lubricant or low-friction material, such as Teflon®, to further facilitate the passage of the tubes 510 through the donor site tissue 100.

The inner diameter of the tube 510 can be selected or structured to approximately correspond to a particular diameter of a micrograft 120 to be removed from the donor site 100, as described herein. According to one exemplary embodiment, the inner diameter of the tube 510 can be less than about 1 mm. For example, 18 or 20 gauge biopsy needles (e.g., having an inner diameter of 0.838 mm and 0.564 mm, respectively) or the like can be used to form the tube 510. A biopsy tube having a larger gauge (and smaller inner diameter) can also be used. Based on the interaction between the tube width or diameter of the harvested micrograft 120 can be slightly smaller than the inside diameter of the apparatus 500 used to harvest it.

A distal end of the tube 510 can be shaped to form a plurality of points 520. For example, the two exemplary points or extensions 520 shown in FIG. 5A can be formed by grinding opposite sides of the tube 510 at an angle relative to the long axis of the tube 510. In a further exemplary embodiment as shown in FIG. 5B, an exemplary apparatus 550 can be provided that includes the tube 510 with three points or extensions 520 provided at a distal end thereof. This exemplary configuration can be formed, e.g., by grinding 3 portions of the tube 510 at an angle relative to the long axis thereof, where the three portions can be spaced apart by about 120 degrees around the perimeter of the tube 510. In still further exemplary embodiments, an apparatus can be provided for harvesting micrografts that includes a tube having more than three points or extensions 520 provided at a distal end thereof, e.g., a tube 510 having four, five, six, seven or eight points 520.

The exemplary points or extensions 520 can facilitate insertion of the apparatus 500, 550 into the tissue at the donor site 100. The exemplary points or extensions 520 that can be formed, e.g., by grinding portions of the distal end of the tube 510 can also have a beveled edge along their sides, which can further facilitate insertion of the apparatus 500, 550 into donor-site tissue. For example, the points or extensions 520 that form a narrow angle at their tip can be inserted into the tissue using a smaller force as compared to points 520 having a larger tip angle, although this force may be applied for a longer distance and/or time to achieve full insertion of the tube 510 into the tissue than that used for tips that have a wider tip angle and thus shorter length of the angled tip region. The initial force needed for the tube 510 to penetrate the tissue can be approximately proportional to the number of points 520 if the angle of each point or extension 520 is held constant. Providing a greater number of points extensions 520 at the distal end of the tube can improve mechanical stability of the tube 510 and/or geometrical control of the severed tissue, but it can use a larger force to penetrate the tissue.

The exemplary apparatus 500 can also included a collar or stop 540 provided on an outer surface of the tube 510. The exemplary stop 540 can be affixed to the tube 510 at a particular distance from the ends of the tips 520, or this distance may be adjustable, e.g., over a range of lengths by moving the stop 540 along the axis of the tube 510.

FIG. 6A illustrates the exemplary apparatus 500 after it is inserted into the tissue at the donor site 100, e.g., until the stop 540 contacts the surface of the donor site 100. A portion of the tissue 600 can be present within a lower portion of the tube 510. Lateral sides of this tissue portion 600 can be cut or severed from the surrounding tissue by the distal end of the tube 510 and/or the points or extensions 520 as the tube 510 penetrates into the donor site tissue 100. Such tissue 600 can remain within the tube 510, and be separated from the donor site 100 to form the micrograft 120, e.g., when the tube 510 is removed from the donor site 100, as shown in FIG. 6B. The exemplary micrograft 120 thus formed can include both epidermal tissue 130 and dermal tissue 140.

The exemplary micrograft 120 can be removed from the apparatus 500, e.g., by providing pressure through an opening 620 at a proximal end of the tube 510 as shown, e.g., in FIG. 6C. Such pressure can be mechanical, hydraulic, pneumatic, etc. For example, the pressure can be provided, e.g., by blowing into the opening, by squeezing a flexible bulb attached thereto, by opening a valve leading from a source of elevated pressure such as a small pump, etc. Alternatively, the exemplary micrografts 120 can be harvested by inserting the exemplary apparatus 500 into a plurality of locations of the donor site 100. Each micrograft 120 within the tube 510 can then push any micrografts above it towards the opening 620. Once the tube 510 has been substantially filled with the harvested tissue, each additional insertion of the exemplary apparatus 500 into the donor site 100 can facilitate pushing of an uppermost micrograft 120 within the tube 510 out of the proximal opening 620.

The exemplary apparatus 500 can be inserted into the donor site tissue 100 to a depth corresponding approximately to a desired length of the harvested micrografts 120. Such distance can be determined and/or controlled, e.g., by appropriate placement or adjustment of the stop 540 on the exemplary apparatus 500. For example, the exemplary apparatus 500 can be configured or structured such that the points or extensions 520 extend to a location at or proximal to the dermal/fatty layer junction 610 as shown in FIG. 6A. For example, the micrograft 120 can be removed from the donor site 100 by removing the apparatus 500 from the donor site without rotating the tube 510 around the axis thereof. In contrast, conventional biopsy needles and the like may require a rotation around the long axis to facilitate removal of tissue samples from the surrounding tissue. The points or extensions 520 provided on the exemplary apparatus 500 can facilitate such removal of the micrograft 120 from the surrounding tissue at the donor site 100.

In certain exemplary embodiments of the present disclosure, some or all of the tissue at the donor site may be cooled, frozen, or partially frozen prior to harvesting the micrografts 120. Such freezing may facilitate cutting, removal, handling, and/or viability of the micrografts 120. The donor site tissue 100 may be cooled or frozen using conventional cooling techniques such as, e.g., applying a cryospray or contacting a surface of the donor site 100 with a cooled object for an appropriate duration. The exemplary apparatus 500 can also be cooled prior to harvesting the micrografts 120. Such cooling and/or freezing can, e.g., increase mechanical stability of the micrografts 120 when they are harvested and/or placed in the matrix 210.

The exemplary micrografts 120 can be provided into the matrix 210 using various techniques. For example, the individual micrografts 120 can be inserted into particular locations of the matrix 210 using, e.g., tweezers or the like. The exemplary apparatus 500 containing a harvested micrograft 120, as shown in FIG. 6B, can also be inserted into a location of the matrix 210, and pressure can be applied to the proximal opening 620 to push the micrograft 120 into the matrix 210. The exemplary apparatus 500 can then be removed from the matrix 210, and the procedure repeated to place a plurality of micrografts 120 in the matrix 210. The proximal opening 620 can be covered while the apparatus 500 is being inserted into the matrix 210 to prevent the micrograft 120 from being pushed further up into the apparatus 500. For example, the upper portion of the tube 510 can be filled with a fluid, e.g., water or a saline solution, to provide an incompressible volume that can further prevent the micrograft 120 from rising further up into the tube 510. Such fluid can also facilitate a removal of the micrograft 120 from the exemplary apparatus 500 by providing pressure at the proximal opening 620.

In a further exemplary embodiment of the present disclosure, an exemplary apparatus 700 can be provided, as shown in FIG. 7. The apparatus 700 can include, e.g., a plurality of the tubes 510 affixed or mechanically coupled to a base 710. The tubes 510 can be provided in various configurations, e.g., in a linear array, or in any one of various two-dimensional patterns along the base 710. The number of the tubes 510 provided in the exemplary apparatus 700 can be, for example, at least 6 tubes 510, more than about 10 tubes 510, or more than about 20 tubes 510. For example, the apparatus 700 can include a linear array of about 3 tubes 510, at least 6 tubes 510, or an array of about 12 tubes 510, e.g., in a rectangular 3×4 array or a 2×6 array. Larger arrays of the tubes 510 can also be provided in further exemplary embodiments of the present disclosure. The spacing of the tubes 510 can be somewhat irregular or varied to avoid formation of recognizable patterns in the donor and/or recipient sites. A larger number of the tubes 510 can be preferable to more rapidly harvest and/or implant a large number of micrografts 120. However, a larger number of the tubes 510 can also correspond to a greater force used to insert the tubes 510 into tissue or a matrix simultaneously, which may be undesirable if the force is too large. Also, the mechanical complexity of the apparatus 700 can increase with a larger number of tubes 510.

A conduit 720 can be provided in communication with proximal openings 620 of the tubes 510. The conduit 720 can also be provided in communication, e.g., with a pressure source 730. For example, the pressure source 730 can include a pump or a deformable bulb or the like. The pressure source 730 can include, e.g., a flexible membrane provided in communication with the conduit 720, such that an elevated pressure can be provided within the conduit 720 when the membrane is deformed. Such configurations can facilitate applying pressure to the proximal openings 620 for removal and/or insertion of the micrografts 120 that can be harvested in the tubes 510, as described herein.

A vibrating arrangement 740 can optionally be provided in the apparatus 700. The vibrating arrangement 740 can be mechanically coupled to the base 710 and/or the tubes 510 to facilitate the insertion of the tubes 510 into the tissue or matrix material for harvesting or placement of micrografts 120. The vibrating arrangement 740 can have an amplitude of vibration in the range of about 50-500 μm, or between about 100-200 μm. The frequency of the induced vibrations can be between about 10 Hz and about 10 kHz, or between about 500 Hz and about 2 kHz, or even about 1 kHz. Particular vibration parameters can be selected based on, e.g., the size, average spacing, and material of the tubes 510, the number of tubes 510 in the exemplary apparatus 700, and/or the tissue being treated. The vibrating arrangement 740 can include circuitry configured to adjust the amplitude and/or frequency of the vibrations.

The exemplary apparatus 700 can be used to simultaneously obtain a plurality of the micrografts 120 in one or more of the tubes 510. Exemplary procedures for obtaining and removing such micrografts 120 using the exemplary apparatus 700 can be similar to the procedures described herein for obtaining single micrografts 120 using the exemplary apparatus 500 shown in FIGS. 6A-6C.

A vibration can also assist in severing tissue proximal to the distal end of the tubes 510 after they are fully inserted into the donor site 100. This can facilitate separation and/or extraction of the tissue portions within the tubes 510 from the donor site 100. These tissue portions can also be held by friction within the tubes 510 as the tubes 510 are withdrawn from the donor site 100.

In further exemplary embodiments of the present disclosure, the donor site tissue can be pre-cooled prior to insertion of the tubes 510, e.g., using convective or conductive techniques such as applying a cryospray or contacting the tissue surface with a cooled object. Cooling of the donor site 100 can reduce a sensation of pain when the tubes 510 are inserted into the donor site tissue 100, and can also make the tissue 100 more rigid and facilitate a more accurate severing of tissue portions (e.g., micrografts 120) by the tubes 510.

The positions and spacing of the tubes 510 in the exemplary apparatus 700 can be determined, e.g., based on characteristics of the micrografts 120 to be obtained, a damage pattern to the donor site 100, and/or other factors as described herein above. The number of the tubes 510 provided in the exemplary apparatus 700 can be selected based on various factors. For example, a larger number of tubes 510 may be desirable to allow more micrografts 120 to be harvested simultaneously from a donor site 100. Such exemplary configuration can facilitate a more efficient harvesting process. A smaller number of the tubes 510 can be easier to insert simultaneously into the donor site tissue 100. Further, the exemplary apparatus 500 having a very large number of the tubes 510 can be challenging to manufacture and/or maintain.

The harvested tissue portions can be deposited directly from the tubes 510 into the biocompatible matrix material 210. The tubes 510 and the tissue portions contained therein can be cooled before removal of the tissue portions. This can stiffen the tissue portions within the tubes 510 and make them easier to manipulate and position.

In a further exemplary embodiment of the present disclosure, an apparatus can be provided that includes a plurality of substantially parallel blades. The ends of certain ones of the adjacent blades can be connected or closed off to provide, e.g., narrow rectangular openings between adjacent blades. Such an exemplary apparatus can be used, e.g., to form the tissue strips 320, such as that shown in FIG. 3C. Spacings, lengths, and other features of this exemplary apparatus can be selected based on factors similar to those described herein, e.g., for the exemplary apparati 500, 700.

In further exemplary embodiments of the present disclosure, the exemplary methods and apparati described herein can be applied to other tissues besides skin tissue, e.g., internal organs such as a liver or heart, and the like. Thus, grafts can be formed for a variety of tissues while producing little damage to a donor site and facilitating rapid healing thereof, while creating graft tissue suitable for placement at recipient sites.

Figure 8A:
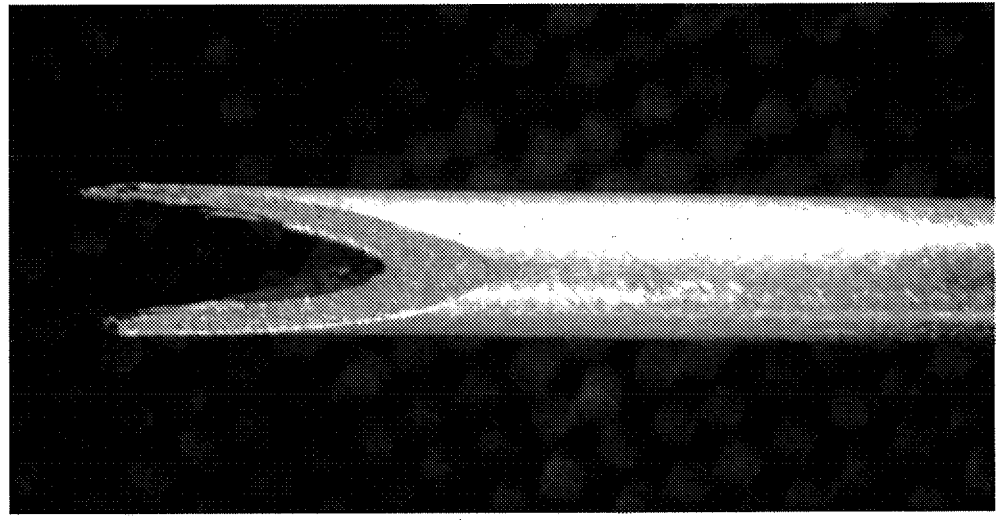
FIG. 8A is an exemplary image of a distal end of the exemplary apparatus that includes two points.
Figure 8B:
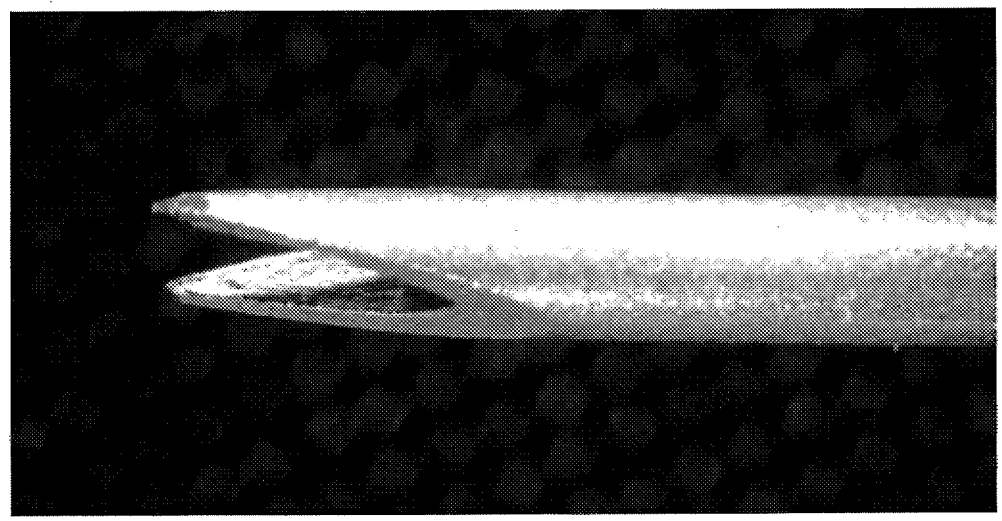
FIG. 8B is a further exemplary image of the distal end of the exemplary apparatus shown in FIG. 8A.

An image of a distal end of an exemplary apparatus that includes two points is shown in FIG. 8A. This exemplary apparatus is similar to the exemplary apparatus 500 illustrated, e.g., in FIG. 5A. A further rotated image of this exemplary apparatus is shown in FIG. 8B. Such exemplary apparatus was formed using a tube having an outside diameter of about 1 mm, and an inside diameter of about 0.5 mm. The points or extensions were formed by grinding two opposite sides of the distal end of the tube at an appropriate angle relative to the axis of the tube. The angle used in the exemplary apparatus shown in FIGS. 8A and 8B was about 30 degrees, although other angles may also be used. A beveled edge of the tube wall can be seen along the sides of the points or extensions. The shape of these points can facilitate insertion of the apparatus into tissue of a donor site and/or separation of a portion of micrograft tissue from the donor site, as described in more detail herein. For example, such micrografts can be separated and removed from the donor site by inserting and withdrawing the apparatus from the donor site tissue without rotating the tube along its axis.

Figure 8C:
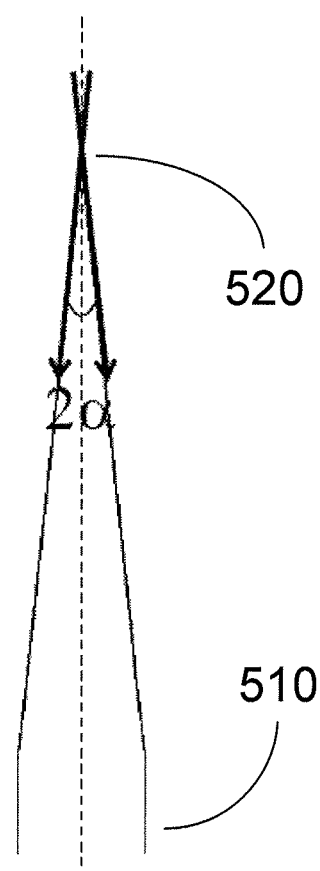
FIGS. 8C and 8D are exemplary schematic illustrations of exemplary geometric parameters that can be associated with the shape of the distal end of the exemplary apparatus shown in FIG. 8A.

The geometry of the distal ('piercing') end of an exemplary tube 510 that includes two points 520 can be characterized by an angle $\alpha$, which represents the angle between each of the opposing lateral sides of the tube 510 that form the points or extensions 520 and the longitudinal axis of the tube 510. The angled lateral sides at the distal end of the tube 510 can each be ground or cut at this angle $\alpha$ relative to the axis of the tube 510, e.g., to form a beveled structure at the distal end of the tube 510. The angle formed at the points or extensions 520 when viewed from the side can thereby be represented by the angle $2a$, as shown in FIG. 8C. For example, the exemplary tip angle of about 30 degrees shown in FIGS. 8A and 8B corresponds to an angle $\alpha$ of about 15 degrees.

Figure 8D:
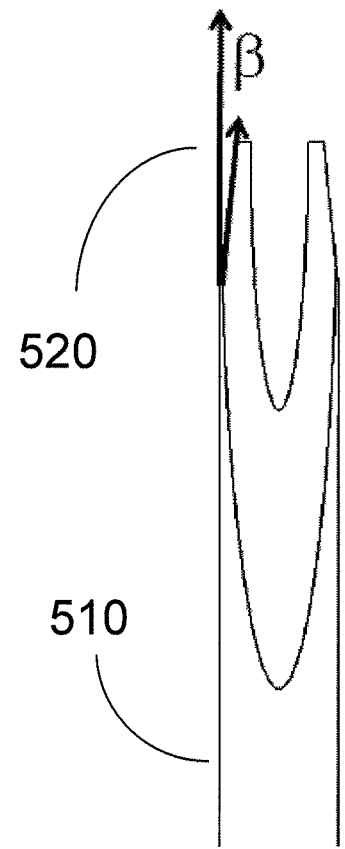

A further beveled surface can be optionally provided in a direction orthogonal to the primary bevel that is characterized by the angle $\alpha$ shown in FIG. 8C. This second bevel can be characterized by an angle $\beta$, which represents the angle at which each of the opposing lateral sides of the tube 510 can be ground or cut relative to the longitudinal axis of the tube 510, as shown in FIG. 8D. This second bevel can be provided to reduce the size or width of the sharp edge of the tips 520 formed at the end of the tube 510.

Figure 8E:
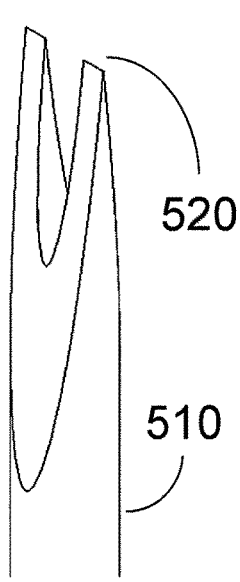
FIGS. 8E-8J are exemplary schematic illustrations of various exemplary geometric configurations that can be provided for the distal end of the exemplary apparatus shown in FIG. 8A.
Figure 8F:
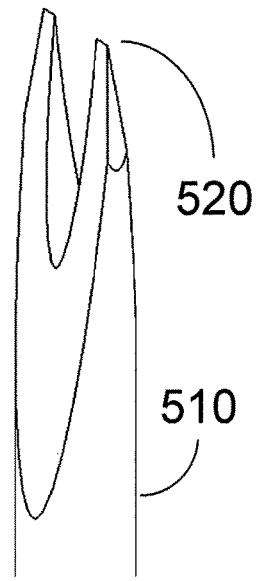
Figure 8G:
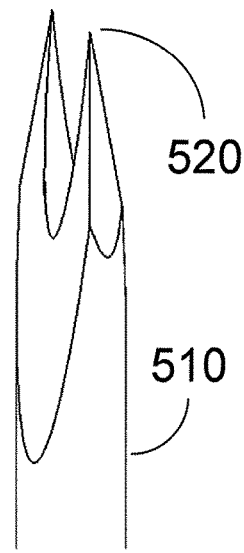

FIGS. 8E, 8F, and 8G illustrate exemplary beveled ends of the tube 510, where the primary bevel angle $\alpha$ can be about 6 degrees. For example, there is no secondary bevel formed in FIG. 8E, and the points or extensions 520 have a flat cutting edge with a length equal to the thickness of the wall of the tube 510. FIGS. 8F and 8G include a secondary bevel, where the angle β corresponding to this secondary bevel is also 6 degrees. The secondary bevel is relatively shallow in the exemplary tip region shown in FIG. 8F, which provides a shorter flat cutting edge at the tips of the points or extensions 520. The secondary bevel is deeper in the exemplary tip region shown in FIG. 8G, such that the tips of the points or extensions 520 form sharp points that can facilitate penetration of tissue more easily.

Figure 8H:
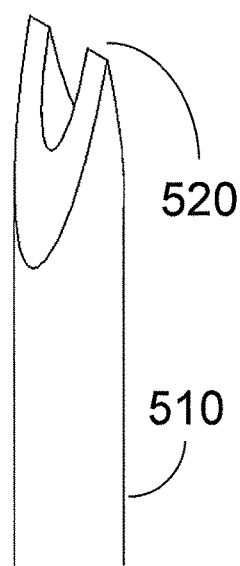
Figure 8I:
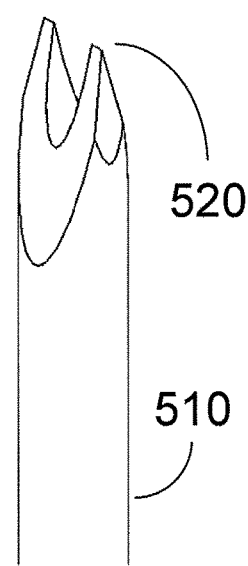
Figure 8J:
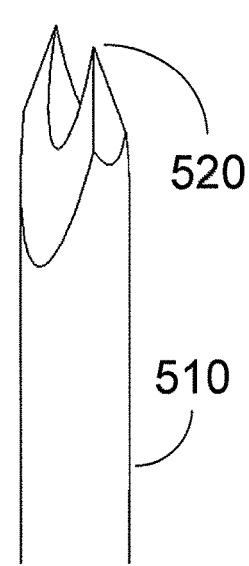

FIGS. 8H, 8I, and 8J illustrate exemplary beveled ends of the tube 510, similar to those shown in FIGS. 8E-8G, but where the primary bevel angle α is 12 degrees. There is no secondary bevel formed in FIG. 8H, a shallow secondary bevel shown in FIG. 8I having an angle β of about 6 degrees, and a deep secondary bevel shown in FIG. 8J, again with an angle β of, e.g., about 0.6 degrees.

The various geometries and points 520 described above and shown in FIGS. 8A-8F can be used in any of the exemplary embodiments of the present disclosure, e.g., for the various devices and methods described herein. For example, the hollow tube 510 can be provided with a bevel angle α of less than about 15 degrees, e.g., about 12 degrees. Such an acute tip angle can provide sharp tips of the points or extensions 520 that can easily penetrate a biological tissue or matrix material. A narrower tip angle α, e.g. about 6 degrees as shown in FIGS. 8E-8G, may be preferable for harvesting and/or implanting micrografts in a denser or tougher tissue or matrix material, where the narrower tips of the points or extensions 520 can be configured to more easily cut through the tissue or matrix material when the tube 510 is inserted therein. A secondary bevel having an angle β, such as the exemplary tips of the points or extensions 520 shown in FIGS. 8F, 8G, 8I, and 8J, can further facilitate insertion of the distal end of the tube 510 into various materials by providing the tips of the points or extensions 520 that are smaller and more pointed. However, the tips of the points or extensions 520 that are sharper and/or narrower, e.g., those having small tip angle α and/or a secondary bevel with angle β, can also be more prone to wear, bending, or other deformation if the tube 510 is repeatedly inserted into tissue or a matrix. Accordingly, the tip geometry selected for a particular application can be selected based on the type of material or tissue the apparatus will be used with, as well as the desired lifetime of the tube 510.

Figure 9:
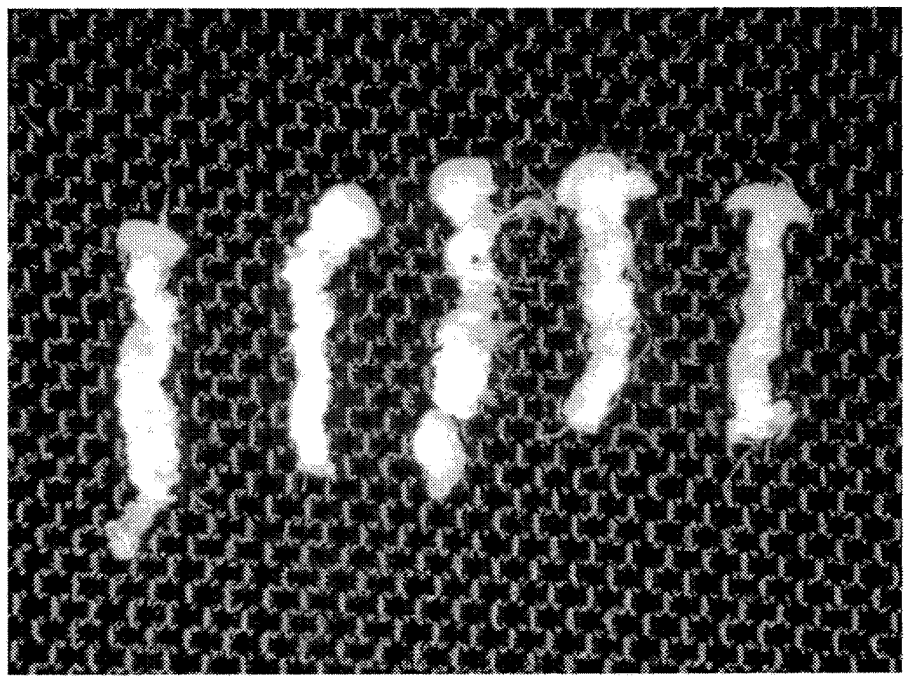
FIG. 9 is an exemplary image of the micrografts obtained using the exemplary apparatus shown in FIG. 8A.

FIG. 9 shows an exemplary image of a plurality of micrografts obtained from a donor site of ex vivo skin tissue using the exemplary apparatus shown in FIGS. 8A-8B. The micrografts are elongated and substantially similar in shape, although details of the shapes may be somewhat irregular. An upper portion of these micrografts includes epidermal tissue, and the lower portion of these micrografts include dermal tissue removed from the donor site. The width of these micrografts is slightly smaller than the internal diameter of the tube 510 shown in FIGS. 8A-8B that was used to harvest them.

The micrografts shown in FIG. 9 were removed from the apparatus by inserting the exemplary apparatus into donor site a plurality of times, until the tube was filled with harvested tissue. Each subsequent insertion of the apparatus into the donor site tissue then forced the uppermost micrograft out of the proximal end of the tube, where it was retrieved individually for analysis. Such micrografts can also be removed by applying pressure to the proximal end of the tube containing the micrograft, to expel it from the distal end of the tube as described herein.

In still further exemplary embodiments of the present disclosure, an apparatus 1000 can be provided, such as that shown in FIG. 10A, which can facilitate harvesting of the exemplary micrografts 120 from the donor site 100 and optionally placing them in a biocompatible matrix 210, as described herein below. The exemplary apparatus 1000 can include a hollow tube 1010 that can include a plurality of points 1020 at the distal end thereof as described herein, which can be similar to the hollow tube 510 shown in FIGS. 5A and 5B.

In one exemplary embodiment of the present disclosure, the tube 1010 can be provided with two points 1020, and the points 1020 can be formed by grinding opposite sides of the distal end of the hollow tube 1010 at an acute angle, e.g., about six degrees, relative to the longitudinal axis of the tube 1010. Such an acute tip angle, e.g., of about 12 degrees or less, can be particularly effective for penetrating and cutting the biological tissue to remove small micrografts 120 therefrom. Such a tube provided with two points 1020 can use a force approximately twice that associated with a single-point needle of similar diameter to penetrate tissue or another material.

Figure 19A:
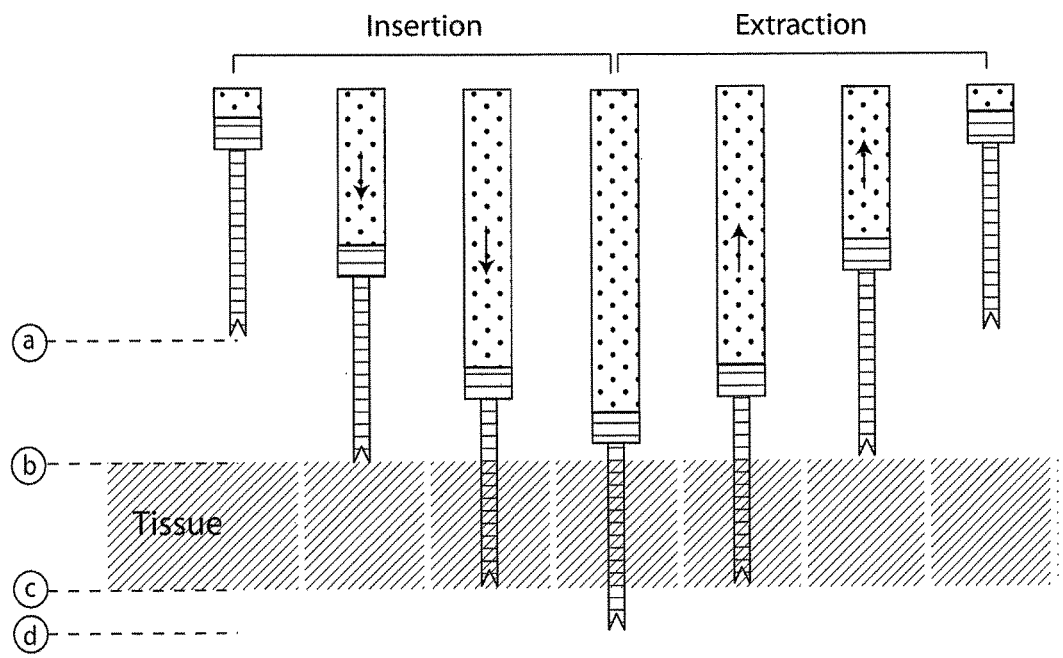
FIG. 19A is a series of illustrations showing an exemplary sequence of insertion and extraction of an exemplary apparatus from a biological tissue using the exemplary apparatus and/or method according to exemplary embodiments of the present disclosure.
Figure 19B:
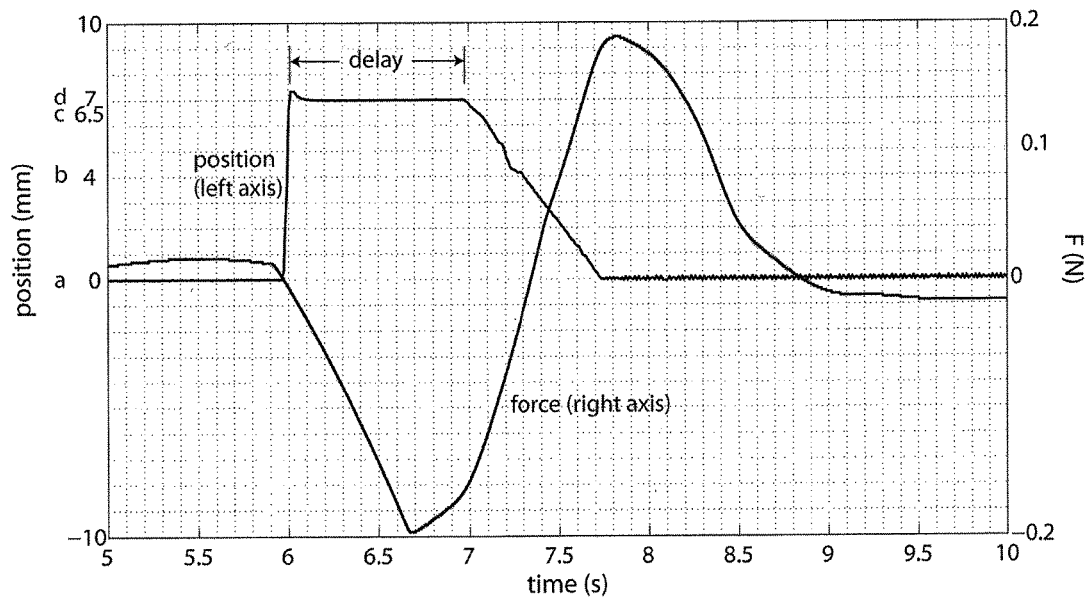
FIG. 19B is a plot of exemplary displacement and force data as a function of time corresponding to the exemplary insertion and extraction sequence shown in FIG. 19A.

For example, FIG. 19A illustrates an exemplary sequence of inserting and extracting or withdrawing a harvesting needle device from a tissue layer. The exemplary needle device can be similar to the hollow pointed tube 510 shown in FIG. 5A, or the exemplary pointed tube 1010 shown in FIG. 10A. A plot of the position of the needle relative to the tissue as a function of time is shown in FIG. 19B, together with a plot of the corresponding force applied to the exemplary needle (e.g., along the longitudinal axis) to perform the insertion and extraction sequence. The needle used to obtain the data shown in FIG. 19B was formed from a 25 gauge tube with a tip bevel angle α of 6 degrees and a side bevel angle β of 6 degrees, similar to the exemplary needle geometry shown in FIGS. 8C, 8D, and 8F.

As provided in the graph of FIG. 19B, the needle can be rapidly inserted through the tissue layer at about 6 seconds and held there for about one second, and then steadily withdrawn to a position outside of the tissue layer over a time span of about 0.8 seconds. There can be an apparent delay in the force needed to maintain the needle at a certain depth after insertion into the tissue, and a residual force on the needle after it is brought to a position outside of the tissue layer. During insertion and extraction of the needle, which was formed using a 25 gauge tube, the maximum and minimum forces observed on the needle were about −0.2 N and 0.2 N, respectively. The delay between movement of the needle in and out of the tissue and the resultant force on the needle may result at least in part from deformation of the tissue as the needle is inserted and withdrawn, and/or some adhesion of the tissue to the needle as the needle is moved relative to the tissue. The small force appearing at the beginning and end of the sequence plotted in FIG. 19B are likely associated with some component friction and/or the vertical load cell sensing attached components.

In one exemplary embodiment of the present disclosure, the tube 1010 can be formed using a 25 gauge thin-wall needle, with an exemplary outer diameter of about 0.51 mm and an internal diameter of about 0.31 mm. This exemplary needle size can be used to harvest micrografts 120 having a width or diameter of about 0.2 mm. The tube 1010 can be formed of any sufficiently strong material that is preferably biocompatible or inert with respect to biological tissue, e.g., a 304 stainless steel, a surgical stainless steel, etc. Further finishing processes can be applied to the tube 1010, such as electropolishing to increase sharpness of the cutting edges or providing a ME-92® chromium coating to increase the material strength. Such finishing processes can increase the cutting effectiveness and/or improve the useful service life of the needle 1010.

Figures 10A, 10B:
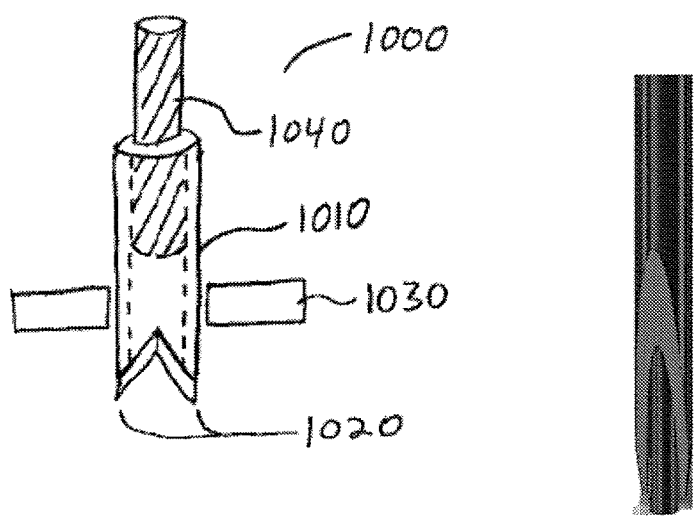
FIG. 10A is a schematic illustration of a portion of an exemplary apparatus that can be used to harvest a micrograft tissue in accordance with further exemplary embodiments of the present disclosure.
FIG. 10B is an illustration of the portion of the exemplary apparatus shown in FIG. 10A.

The tube 1010 can be slidably attached to a substrate 1030, such that the tube 1010 passes through a hole provided in the substrate 1030, as shown in FIG. 10A. The position of the tube 1010 relative to the substrate 1030 can be controlled by a positioning arrangement that can controllably translate the tube 1010 relative to the substrate 1030, e.g., substantially along the longitudinal axis of the tube 1010. In this manner, the distance that the distal end of the tube 1010 protrudes past the lower surface of the substrate 1030 can be controllably varied.

The exemplary apparatus 1000 further includes a pin 1040 provided in the central lumen or opening of the tube 1010. The diameter of the pin 1040 can be substantially the same as the inner diameter of the tube 1010 or slightly smaller, such that the pin 1040 can be translated along the axis of the tube 1010 while filling or occluding most or all of the inner lumen of the tube 1010. The pin 1040 can be formed of a low-friction material, or coated with a low-friction material such as, e.g., Teflon® or the like, to facilitate motion of the pin 1040 within the tube 1010 and/or inhibit accumulation or sticking of biological material to the pin 1040. The distal end of the pin 1040 can be substantially flat to facilitate displacement of a micrograft 120 within the tube 1010 when the pin 1040 is translated.

In one exemplary embodiment of the present disclosure, the tube 1010 can be formed using a 25 gauge thin-wall needle, with an exemplary outer diameter of about 0.51 mm and an internal diameter of about 0.31 mm. This exemplary needle size can be used to harvest micrografts 120 having a width or diameter of about 0.2 mm. A pin 1040 that can be used with a tube 1010 of this size can have an outer diameter of about 0.24 mm. The difference between the inner diameter of the tube 1010 and the diameter of the pin 1040 can facilitate motion of the pin 1040 within the tube 1010, whereas the pin is sufficiently wide to push a micrograft 120 out from the interior of the tube 1010. The tube 1010 and/or the pin 1040 can be formed of any sufficiently strong material that is preferably biocompatible or inert with respect to biological tissue, e.g., a 304 stainless steel, a surgical stainless steel, etc.

The pin 1040 can be provided with a further positioning arrangement that can controllably translate the pin 1040 relative to the tube 1010 e.g., substantially along the longitudinal axis of the tube 1010. In this manner, the position of the distal end of the tube 1010 relative to that of the distal end of the pin 1040 can be controllably varied. For example, the location of the distal ends of both the tube 1010 and the pin 1040 relative to that of the lower surface of the substrate 1030 can preferably be controllably and independently selected and varied.

An exemplary illustration of the tube 1010 and pin 1040 as described herein is shown in FIG. 10B, which shows the pin 1040 positioned relative to the tube 1010 such that their distal ends are substantially aligned. Portions of the pin 1040 and/or tube 1010 can optionally be provided with a coating or surface treatment to reduce friction between them and/or between either component and biological tissue. Exemplary coatings that can be used include a plastic or polymer, e.g. nylon or polyethylene, a polished metal alloy, or the like.

Figure 11:
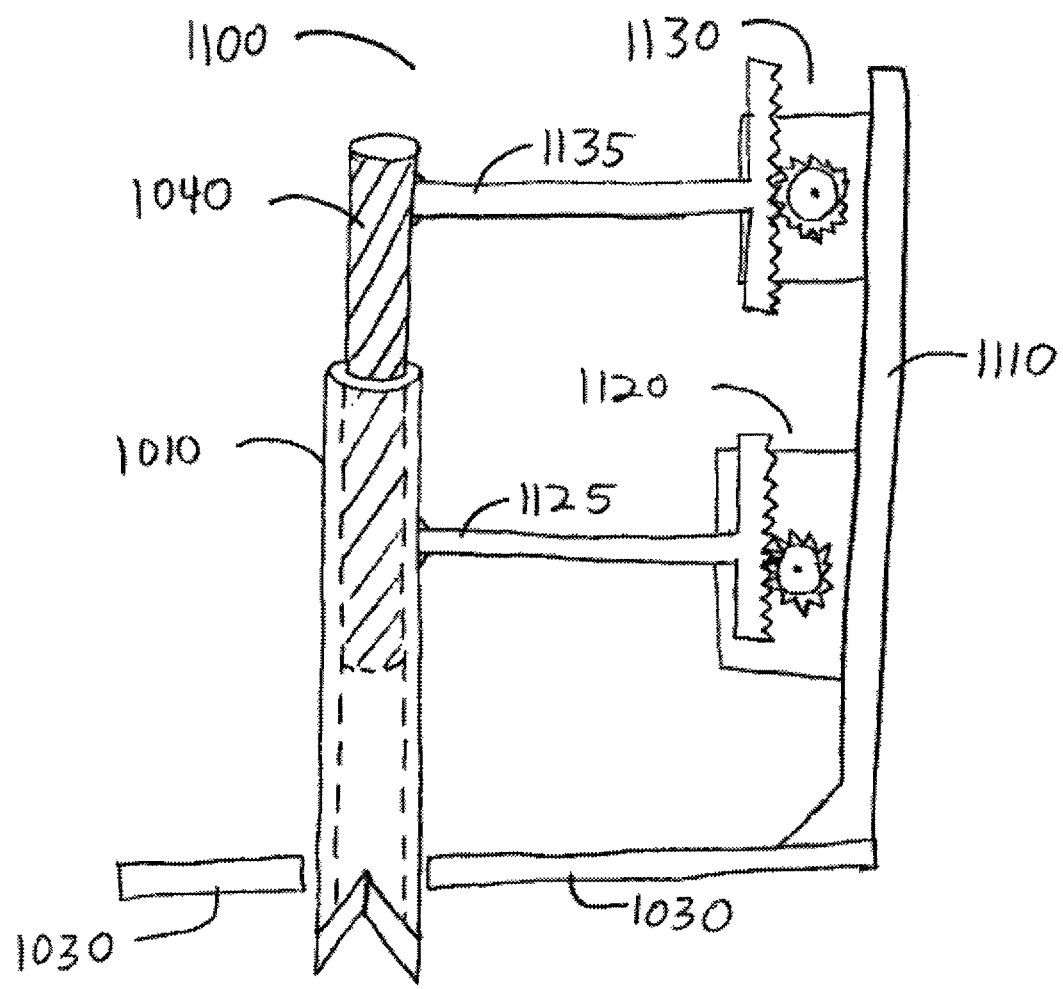
FIG. 11 is a schematic illustration of an exemplary apparatus that can be used to harvest the micrograft tissue in accordance with still further exemplary embodiments of the present disclosure.

A schematic side view of an exemplary apparatus 1100 that can be used to facilitate harvesting of the exemplary micrografts 120 from the donor site 100 and optionally placing them in a biocompatible matrix 210 is shown in FIG. 11. The apparatus 1100 can include the tube 1010, pin 1040, and substrate 1030 shown in FIG. 10A. A plate 1110 or other supporting structure can be affixed to the substrate 1030, or optionally provided with the substrate 1030 as a single unitary component.

A first actuator 1120 can be affixed to the plate 1110, and mechanically coupled to the tube 1010 using a first coupling arm 1125 or the like. Similarly, a second actuator 1130 can be affixed to the plate 1110, and mechanically coupled to the pin 1040 using a second coupling arm 1135 or the like. The first actuator 1120 and second actuator 1130 can be conventional linear actuators or the like. Such actuators 1120, 1130 can include appropriate controls such that the locations of the coupling arms 1125, 1135 relative to the plate 1110 (and substrate 1130) can be controllably positioned and varied independently. For example, the linear range of motion of the actuators 1120, 1130 can be about 2 cm or less for many typical uses of the apparatus 1100, e.g., for harvesting micrografts of skin tissue and placing them in a matrix as described herein below.

In the exemplary schematic configuration of the apparatus 1100 shown in FIG. 11, the translation or positioning range of the actuator 1120 can be selected such that the distal end of the tube 1010 can be raised above the lower surface of the substrate 1030, and lowered such that the distal end protrudes to a maximum distance of about 1-2 cm below the lower surface of the substrate 1030. Similarly, the positioning range of the actuator 1130 can be selected such that the distal end of the pin 1040 can be raised above the distal end of the tube 1010 by a distance of about 1-2 cm, and lowered such that the distal end of the pin 1040 is substantially aligned with the distal end of the tube 1010 (e.g., aligned with the tips of the points 1020). The translation range of the actuators 1120, 1130 can also be greater than these exemplary distances, for example, if the donor tissue being harvested is relatively thick. Alternatively, these translation ranges may be somewhat smaller if micrografts are being harvested from thin layers of tissue and optionally placed in a thin matrix.

Figure 12:
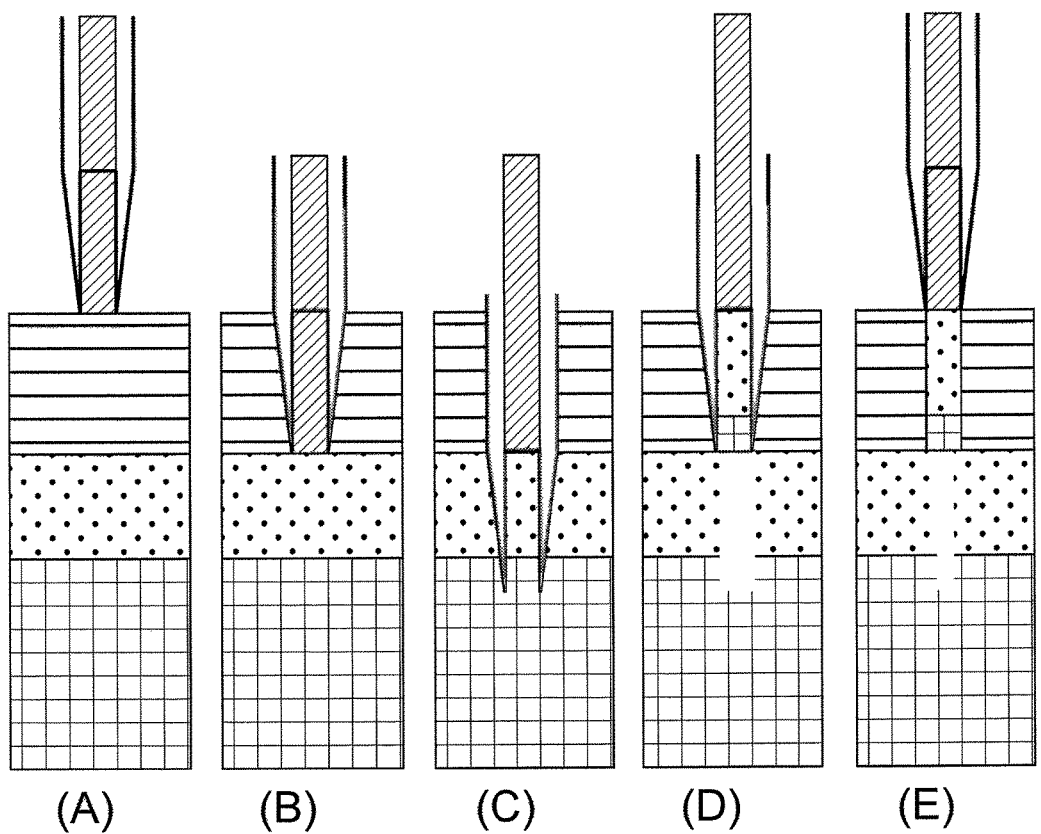
FIG. 12 is a schematic illustration of an exemplary sequence of procedures that can be used to the harvest micrograft tissue in accordance with further exemplary embodiments of the present disclosure.

An exemplary sequence for harvesting a micrograft 120 from a donor site 100 and placing it in a matrix 210 in accordance with embodiments of the present disclosure is shown in FIGS. 12A-12E. As an initial matter, the surface of the donor site can be cleaned, sterilized, shaved, and/or otherwise prepared, and a portion or sheet of a matrix material 210 can be placed thereon, as shown in FIG. 12A. The distal ends of the tube 1010 and the pin 1040 can be aligned by the respective actuators (not shown), and positioned proximal to the upper surface of the matrix 210. The tube 1010 and the pin 1040 can be translated such that the distal ends thereof penetrate or pass through the thickness of the matrix 210, and are positioned proximal to the surface of the donor site 100 as shown in FIG. 12B. The tube 1010 and pin 1040 can push aside a small amount of the matrix material, which can be viscous, pliable, elastic, or the like, as they pass through the matrix 210.

The tube 1010 can then be translated downward such that it penetrates into the tissue of the donor site 100, while the position of the pin 1040 can be held substantially stationary relative to the donor site 100 such that its distal end remains positioned proximal to the surface of the donor site 100, as shown in FIG. 12C. The distal end of the tube 1010 can sever a portion of the tissue from the surrounding tissue at the donor site as the tube 1010 penetrates the donor site, such that a portion of tissue from the donor site 100 can be located within the distal end of the lumen of the tube 1010.

The depth of penetration of the tube 1010 into the donor site 100 can be controlled by the tube actuator 1120, as shown in FIG. 11. The tube 1010 can be translated such that the distal end thereof is located at a particular depth within the donor site tissue. For example, if the donor site is skin tissue, the distal end of the tube 1010 can be extended such that it is proximal to the lower end of the dermis layer, e.g., such that it penetrates slightly into the underlying fatty tissue as shown in FIG. 12C.

The tube 101 and pin 1040 can then be lifted or retracted simultaneously such that they substantially maintain their relative positions until the distal end of the tube 1010 is proximal to the surface of the donor site 100 or slightly above it, as shown in FIG. 12D. The portion of tissue severed from the donor site 100 by the tube 1010, which can be used as a micrograft 120, can also be held within the distal end of the tube 1010, such that it is lifted or removed from the donor site 100 as the tube 1010 is withdrawn therefrom. If the tissue being harvested is skin tissue, removal of the micrograft 120 from the donor site can be facilitated if the tube 1010 first penetrates to at least an upper surface of the subdermal fatty layer. The lower end of the micrograft 120 can be more easily detached or torn away from adjacent fatty tissue than from dermal tissue.

As shown in FIG. 12D, s withdrawal of the tube 1010 and the pin 1040 together from the donor site 100 can place the micrograft 120 within the layer of the matrix material 210. For example, the tube 1010 and the pin 1040 can be raised substantially simultaneously such that the distal end of the tube 1010 is positioned proximal to the lower surface of the matrix material 210 or within the matrix material 210. The tube 1010 can then be further retracted from the matrix 210 while holding the location of the pin 1040 substantially stationary relative to the matrix 210, as shown in FIG. 12E. This exemplary procedure facilitates placement of the micrograft 120 substantially within the material of the matrix 210 using the pin 1040 as the tube 1010 is retracted from around the micrograft 120. In this manner, the micrograft 120 can be placed within the matrix 210 and remain there, while the tube 1010 and the pin 1040 are completely removed from the donor site 100 and matrix 210.

The exemplary apparatus shown in FIG. 11 and the tissue harvesting sequence shown in FIGS. 12A-12D and described herein provide several advantages for harvesting micrografts 120 from the donor site and placing them in the matrix 210 to facilitate their use in grafting or autografting procedures. For example, the micrograft 120 can be positioned within the matrix 210 without being exposed to open air (or another intermediate environment) to reduce a chance of contamination, biological stress, etc. The various penetration depths can be selected or adjusted based on the desired depth of the micrografts to be harvested, the thickness of the matrix material 210 to be used, etc. The micrografts 120, which may be difficult to manipulate because of their small size and/or soft tissue consistency, can be placed in the matrix 210 in substantially the same orientation as they had within the donor site.

The substrate 1030 shown in FIG. 11, if present, can provide a mechanical stabilization to the matrix 210 and a surface of the donor site 100 when the apparatus 1100 is placed over the layer of matrix material 210. Placing the substrate 1030 over the matrix 210, if present, and/or the donor site 100 can inhibit motion and/or deformation of the matrix 210 and tissue of the donor site 100 while the micrografts 120 are being harvested.

Figure 13A:
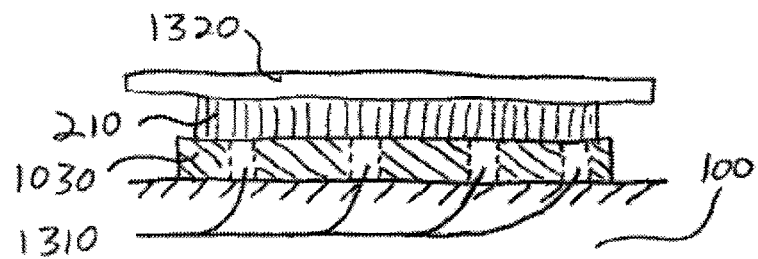
FIG. 13A is a schematic illustration of an exemplary configuration of a stabilizing substrate that can be used to harvest the micrograft tissue in accordance with further exemplary embodiments of the present disclosure.
Figure 13B:
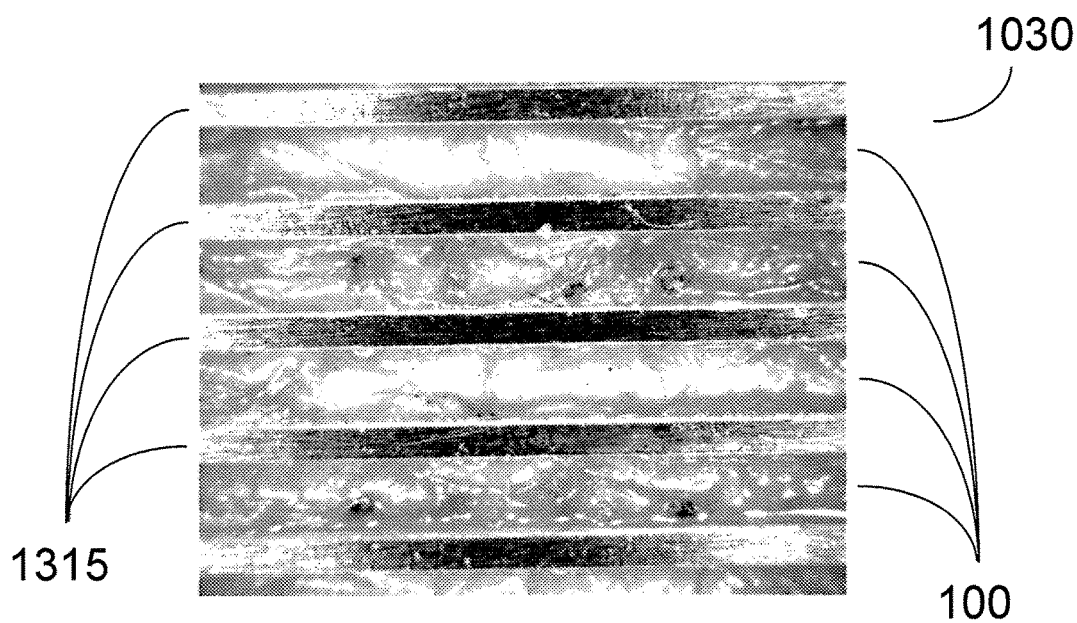
FIG. 13B is an exemplary image of a further exemplary configuration of a stabilization substrate in accordance with yet further exemplary embodiments of the present disclosure.

In a further exemplary embodiment of the present disclosure, the substrate 1310 can include a plurality of strips or slats 1315, as shown in FIG. 13B, with elongated openings between them. The black dots shown in FIG. 13B are micrografts that were harvested from a donor site that was colored black, and implanted into the recipient site shown in this figure. Both the donor and recipient sites were skin tissue of a pig, creating an allograft. The substrate 1030 can be placed over the donor tissue 100 as described above to stabilize the tissue 100, while the harvesting tubes 510, 1010 can be inserted into the tissue 100 between the slats 1315. The substrate 1310 can also be used to facilitate positioning of the tubes 510, 1010 relative to the donor tissue, e.g., for repeated insertions and extractions of the tube 510, 1010 from a region of donor tissue 100. The substrate 1030 can also be provided with other geometrical shapes and arrangements of openings therethrough, such as a plurality of openings having an elliptical, triangular, square, or other shape, or a combination thereof.

In a further exemplary embodiment of the present disclosure, the substrate 1030 can be placed directly on the surface of the donor site 100 to provide mechanical stabilization and reduce movement of the tissue of the donor site 100, as shown in FIG. 13. The substrate 1030 can be provided with one or more holes 1310 therethrough. One or more of the tubes 1010 can be configured to pass through the holes 1310 to sever and extract micrografts 120 from the donor site, e.g., as described above and illustrated in FIGS. 12A-12E. The matrix 210 can be provided on top of the substrate 1030 as shown in FIG. 13A. Optionally, a layer of dressing material 1320 or the like can be placed on the top surface of the matrix 210 to further stabilize the matrix 210 and/or facilitate handling of the matrix 210. If the substrate 1030 is provided between the matrix 210 and the donor site, as shown in FIG. 13A, the translation distances or heights of the tube 1010 and pin 1030 shown in the sequence of FIGS. 12A-E can be controlled appropriately such that the micrografts 120 are harvested from the donor site 100 and deposited in the matrix 210 above the substrate 1030.

Figure 14:
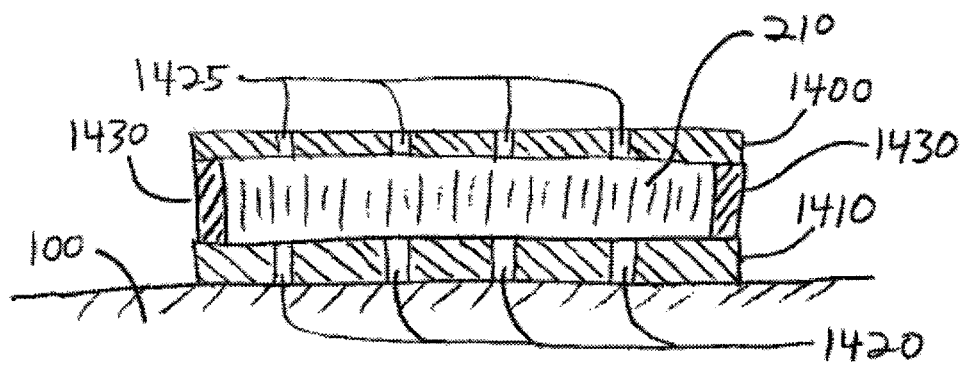
FIG. 14 is a schematic illustration of an exemplary configuration of an arrangement that includes two stabilizing substrates that can be used to harvest the micrograft tissue in accordance with additional exemplary embodiments of the present disclosure.

In a further exemplary embodiment of the present disclosure, two substrates 1400, 1410 can be used to provide further stabilization, as shown in FIG. 14. A lower substrate 1410 having one or more holes 1420 therethrough can be provided on the surface of the donor site 100, similar to the substrate 1030 shown in FIG. 13A. The matrix 210 can be provided on top of the lower substrate 1410. An upper substrate 1400 can be provided on top of the matrix 210 or dressing material 1320, if present. Such upper substrate 1400 can be provided with one or more holes 1425 therethrough, which can correspond to and/or be aligned with the holes 1420 provided in the lower substrate 1410. These aligned holes 1420, 1425 can facilitate translation of the tube 1010 into and out of the matrix 210 and donor site tissue 100 while providing mechanical stability to both the donor site 100 and the matrix 210. Such aligned holes 1420, 1425 in the lower substrate 1410 and upper substrate 1400 can also provide a further mechanical stability and an improved alignment of one or more of the tubes 1010 as they are translated vertically through the holes 1420, 1425.

In a still further exemplary embodiment of the present disclosure, a barrier 1430, e.g. a sidewall or the like, can be provided between the lower substrate 1410 and the upper substrate 1400 as shown in FIG. 14, e.g., proximal to the perimeter of one or both substrates. The lower substrate 1410, the upper substrate 1400, and the barrier 1430 can together form an enclosure around the matrix 210. This exemplary configuration can facilitate containment of the matrix 210, e.g., if the matrix 210 is formed from a viscous or easily deformable material. Accordingly, the exemplary embodiment of the present disclosure shown in FIG. 14 can facilitate a placement of micrografts 120 into the matrix 210 that may likely not be mechanically rigid or stable. The exemplary embodiment shown in FIG. 14 may be used with other various embodiments of the present disclosure described herein.

The exemplary apparatus 1100 can be used to harvest a plurality of micrografts 120 from the donor site 100, and optionally place them in the matrix 210. For example, the substrate 1030 can be provided with a plurality of spaced-apart holes therethrough. The plate 1110 shown in FIG. 11, or another portion of the apparatus 1100 supporting the tube 1010 and pin 1040, can be configured or structured to be translatable over the substrate 1030, such that the tube 1010 and pin 1040 can be positioned over a plurality of holes in the substrate 1030. Such translation can be in one dimension (e.g., linear) or in two dimensions, e.g., over a particular surface region of the substrate 1030. In this exemplary manner, a plurality of micrografts 120 can be harvested from a donor site 100 and placed in a plurality of locations in the matrix 210, e.g., proximal to a plurality of the holes in the substrate 1030, while maintaining the substrate 1030 and the exemplary apparatus 1100 in a single location relative to the donor site 100.

In a further exemplary embodiment of the present disclosure, the apparatus 1100 shown in FIG. 11 can be provided with a plurality of the tubes 1010 and of the pins 1040. All of the tubes 1010 can be translatable together using a single first actuator 1120, or certain ones of the tubes 1010 can be translated simultaneously and/or sequentially using a plurality of the first actuators 1120 and appropriate first coupling arms 1125. Similarly, the plurality of pins 1040 can be translatable together using a single second actuator 1130, or certain ones of the pins 1040 can be translated simultaneously and/or sequentially using a plurality of second actuators 1130 and appropriate second coupling arms 1135. In general, it may be preferable for the translation of each of the tubes 1010 to be coordinated with its associated pin 1040 (i.e., the pin 1040 provided in the lumen of the particular tube 1010). In this exemplary manner, each combination of the tube 1010 and the associated pin 1040 can be controlled to perform the exemplary harvesting and implanting sequence illustrated in FIGS. 12A-12E.

The matrix 210 containing one or more micrografts 120 as described herein can be used as a graft material that can be placed over a recipient site of damaged tissue that has been suitably prepared. In general, this graft material will include a plurality of micrografts 120 that are provided in the matrix 210. The spacing of the micrografts 120 in the matrix 210 can be selected to facilitate the micrografts to grow within or through the matrix 120 and eventually provide sufficient coverage and/or repair of the damaged region. The micrografts 120 can be placed in the matrix 210 in a uniform pattern, randomly, or in any other desired spatial arrangement. In certain exemplary embodiments of the present disclosure, the density or spacing of the implanted micrografts 120 can vary in different regions of the matrix 210. For example, a higher density and/or smaller spacing of the micrografts 120 can be provided closer to the edges of the matrix 210 to improve peripheral integration and/or revascularization of the graft. A sterile dressing or the like can be placed over the graft material after it is placed on the damaged region of tissue. Such dressing can be adhered to the graft material to facilitate handling and positioning of the graft material on the recipient site.

In a further exemplary embodiment of the present disclosure, the harvested micrografts 120 can be introduced or transplanted directly into, e.g., substantially whole tissue at the recipient site. For example, the micrografts 120 can be harvested from the donor site 100 that may contain melanocytes, and inserted directly into tissue at a recipient site that lacks sufficient melanocytes. Such exemplary procedure can be used to repigment skin tissue, e.g., to treat vitiligo or similar conditions. Tissue at the recipient site 100 can also be frozen or partially frozen, as described herein, prior to insertion of micrografts 120 therein.

An exemplary apparatus 1500 for implanting micrografts 120 into a recipient site 1510 is shown in FIGS. 15A-15E. The apparatus 1500 can include the hollow tube 1010 that can include a plurality of the points 1020 at the distal end thereof, and the pin 1040 provided in the central lumen or opening of the tube 1010, similar to the apparatus shown in FIG. 10A. The exemplary apparatus 1500 can further include a hollow piercing needle 1520 that can be provided around the tube 1010, as shown in FIG. 15, such that the tube 1010 can be advanced and/or retracted within the piercing needle 1520. The piercing needle 1520 can include a single point 1525 configured to pierce and penetrate a biological tissue. The piercing needle 1520 can be manually controlled, or it can be controlled using an actuator, e.g., similar to the actuators 1120, 1130 in the exemplary apparatus 1100 shown in FIG. 11.

In an exemplary method of the present disclosure, the tube 1010 and the pin 1040 can be used to harvest a tissue micrograft 120, for example, using the exemplary harvesting sequence shown in FIGS. 12A-D. The micrograft 120 can be retained in the tube 1010 when the tube 1010 and pin 1040 are fully withdrawn from the donor site 100. The tube 1010 and the pin 1040 can be located within the piercing tube 1520 such that the distal end of the tube 1010 is within the piercing needle 1520, as shown in FIG. 15A.

The piercing needle 1520 can then be advanced into the recipient site 1510, such that the point 1525 of the piercing needle 1520 separates a portion of the tissue in the recipient site 1510 as shown in FIG. 15B. The tube 1010 and pin 1040, together with the micrograft 120, can be advanced forward together with the piercing needle 1520 such that the distal end of the tube 1010 containing the micrograft 120 is located below or proximal to the surface of the recipient site 1510, as shown in FIG. 15B. The piercing needle 1520 can be withdrawn from the recipient site 1510 while holding the tube 1010 substantially stationary relative to the recipient site 1510, such that the distal end of the tube 1010 containing the micrograft 120 is located within the separated tissue of the recipient site 1510, as shown in FIG. 15C.

Figure 15E:
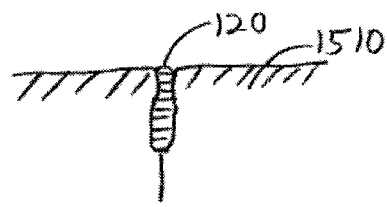

The tube 1010 can then be withdrawn from the recipient site 1510 while holding the pin 1040 substantially stationary relative to the recipient site 1510, such that the micrograft 120 remains within the separated tissue of the recipient site 1510 when the tube 1010 is withdrawn, as shown in FIG. 15D. Upon removal of the apparatus 1500 from the recipient site 1510, the micrograft 120 can remain within the recipient site 1510 in a known orientation, as shown in FIG. 15E.

Such direct implantation can be used for tissue normalization, e.g., to treat vitiligo by transplanting the micrografts 120 containing melanin directly into a depigmented recipient site 220. The exemplary micrografts 120 can also be harvested from a healthy donor site 100 and placed directly into the recipient site 1510 that includes scar tissue to facilitate growth of healthy tissue in the scar using the exemplary method and apparatus shown in FIGS. 15A-5E. In a further exemplary embodiment of the present disclosure, portions of tissue can be removed from the recipient site 1510 prior to placing micrografts 120 in holes that are formed at the recipient site 1510 by the removal of these tissue portions. The holes can be about the same size or slightly larger than the size of the micrografts 120 to be inserted therein, to facilitate such insertion. The holes can be formed at the recipient site, e.g., using one or more of the tubes 510 as described herein, by removing or ablating the tissue using, e.g., an ablative laser, etc.

The exemplary method and apparatus illustrated in FIGS. 15A-15D can be used for a variety of procedures, including grafting between or among various tissues besides skin, such as, e.g., muscle tissue, organ tissue, etc. "Hybrid" or heterogeneous grafts involving different tissues can also be generated using the exemplary methods and apparatus described herein. For example, the micrografts 120 from the donor site having a first tissue type can be placed in a second type of tissue at a donor site. Such exemplary grafting procedures can be used in many different applications. For example, micrografts 120 from an endocrine organ can be placed in a donor site 1510 that includes skin. For example, pancreatic tissue micrografts can be placed in skin tissue to provide for insulin secretion. As another example, smooth muscle tissue can be introduced into the gastrointestinal tract. Micrografts 120 obtained from other functional tissues may be placed in donor sites having different characteristics.

In certain exemplary embodiments of the present disclosure, the piercing needle 1520 can be provided around at least a portion of the tube 510, 1010 without a sharpened point 1525. The distal end of the piercing needle 1520 can be flat, for example, and the outside of the distal end may optionally be widened or flanged. Such a piercing needle 1520 can serve as a guide and/or support for the tube 510, 1010, and can reduce or prevent bending, distortion, breakage, etc. of the tube 510, 1010 when it is inserted into and withdrawn from a donor tissue site. It can also facilitate control of the insertion depth of the tube 1010 and/or the pin 1040 (if present) in the tissue.

In further exemplary embodiments of the present disclosure, a conduit can be provided in communication with the lumen of the tubes 510, 1010 described herein, e.g., connected to a proximal end of the tubes 510, 1010. Such conduit can be configured similar to the conduit 720 shown in FIG. 7. The conduit can also be provided in communication with a source of low and/or high pressure, e.g., a vacuum arrangement and/or a source of pressurized gas or liquid. For example, the diameter of the pin 1040 can be sized slightly smaller than the internal lumen diameter of the tube 1010. Such a configuration can facilitate a fluid such as a gas to pass through the lumen of the tube 1010 around the pin 1040, and further allow pressure differentials to propagate through the lumen of the tube 1010. A controlled application of low pressure from the conduit to the lumen of the tube 1010 can facilitate a separation of the micrografts 120 from surrounding tissue. Similarly, an application of an elevated pressure from the conduit into the lumen of the tube 1010 can facilitate removal or expulsion of a micrograft 120 from the tube 1010 after it is harvested.

In a further exemplary embodiment of the present disclosure, a fluid can be provided within the tube 510 shown in FIGS. 5A and 5B or the tube 1010 shown in FIG. 10A, e.g., such that a portion of the fluid is present between the tube 1010 and the pin 1040. This fluid can reduce friction between the pin 1040 and the tube 1010. The fluid can also reduce or prevent a buildup or accumulation of biological tissue proximal to the distal end of the tube 1010 when the tube 1010 is used to harvest a plurality of tissue micrografts 120. The fluid can also facilitate a retention of the micrografts 120 in the tube 1010 and/or release of the micrografts 110 from the tube, e.g., by providing the fluid at a reduced or elevated pressure during appropriate steps in the exemplary micrograft manipulation sequences shown, e.g., in FIGS. 6A-6C, 12A-12E, and/or 15A-15D. For example, the fluid can improve the accuracy of placement of the micrografts 120 in tissue 1510 at the donor site or in the matrix 210 as described herein. Such accuracy in positioning the harvested micrografts 120 can, e.g., reduce or prevent a formation of cysts or other undesirable results when the micrografts 120 are allowed to grow after harvesting.

Such fluid can be provided, e.g., through a conduit or the like that can be provided in communication with a proximal end of the tube 1010, similar to the conduit 720 shown in FIG. 7. Alternatively, the fluid can be provided through an opening formed in the side of the tube 1010, etc. If the piercing needle 1520 is used, such as provided in the exemplary apparatus 1500 shown in FIG. 15, the fluid can also or alternatively be provided between the piercing needle 1520 and the tube 1010.

Exemplary fluids that can be used can be biocompatible, inert with respect to the biological tissue, etc. Such fluid preferably would not produce any adverse effect when contacting the tissue 100, 1510. For example, the fluid may include a saline solution, glycerol, or the like. It may be buffered, and can include one or more additional components, such as anticoagulants, antibacterial agents, coagulants, etc. One or more growth factors can also be added to this fluid to expose the micrografts 120 to such growth factors before implanting them in the matrix 210 or directly into the recipient site 220, which can enhance the viability of the micrografts 120.

Force sensors, optical sensors, and/or position sensors can optionally be provided in communication with the actuators 1120, 1130 and/or the tubes 510, 1010 and/or pin 1040, to improve control of the exemplary harvesting and/or matrix implantation procedures described herein. For example, such sensor can be used to detect penetration depths and/or penetration resistance of the tube 101 and/or the pin 1040 to assist in harvesting and/or implanting particular layers of tissue and/or sizes of the micrografts 120.

A sensor for detecting the presence of micrografts within the tube 510, 1010 can also be provided. Such sensor can include, e.g., a source of a small electric current provided to the tube 510, 1010 that is configured to detect an electrical resistance or change in resistance within the tube 510, 1010. For example, a detected resistance when a small current is flowed to the needle 510, 1010 (e.g., in an electrode configuration) can indicate whether the needle 510, 1010 is empty or if a micrograft 120 is present therein. Alternatively, a laser fiber and a photodetector may be provided within the needle to optically detect changes in scattered light, indicating whether or not the micrograft 120 is present.

Such micrograft sensor could be used, for example, to determine the number or percentage of actual micrografts harvested and/or implanted by the tube 510, 1010, e.g., if a plurality of such micrografts is processed in a two-dimensional scan or traversal of the donor site 100 and/or the recipient site 1510. A relatively small number of "missed" micrografts may be acceptable in a certain procedure, whereas a larger number or percentage of "missed" micrografts can indicate, e.g., that the needle 510, 1010 needs to be replaced, that the graft material is not viable or acceptable, and/or that the procedure should be repeated or continued. If detected "missed" micrografts are localized in the donor site 100, this could indicate that the tissue might be structurally different in a particular region, e.g., a mole or small scar can be present in the donor site 100.

Figure 16:
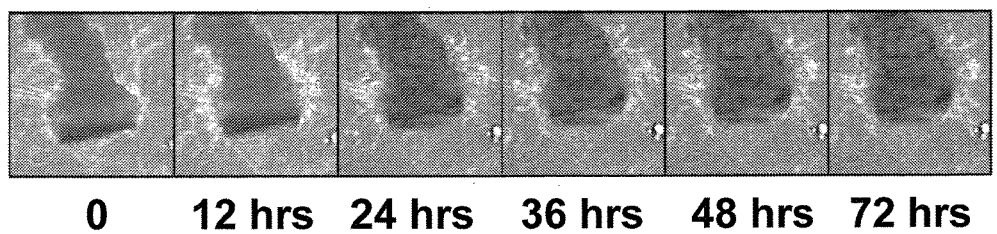
FIG. 16 is a series of exemplary images of a micrograft harvested from pig skin placed in a collagen gel matrix using the exemplary apparatus and/or method according to exemplary embodiments of the present disclosure.

An exemplary set of images of the micrograft that was collected from pig skin and placed in a collagen gel is shown in FIG. 16. The epidermal portion of the micrograft is the darker area at the lower end of the micrograft in these images. Even at times as short as 12 hours (second image from the left in FIG. 16), live cells can be observed migrating from the micrograft into the surrounding gel matrix, as indicated by the lighter areas around the dark micrograft. This migration is observed to continue 72 hours after placing the micrograft into the collagen gel (rightmost image in FIG. 16), indicating that the micrografts that are harvested and placed in a matrix, in accordance with exemplary embodiments of the disclosure described herein, can be viable for extended times and can provide viable graft material.

Figure 17:
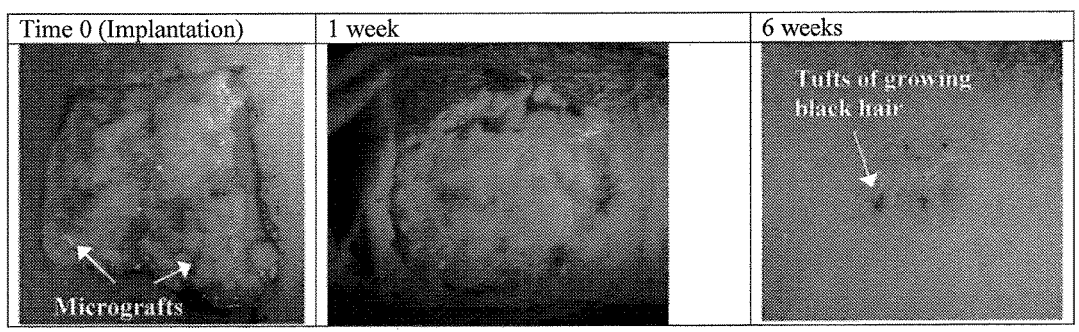
FIG. 17 is a series of exemplary images of micrografts harvested from a black mouse and implanted in a wound formed in a nude mouse using the exemplary apparatus and/or method according to exemplary embodiments of the present disclosure.

In further exemplary embodiments of the disclosure, micrografts 120 can be implanted into cleaned wound area 220 without the matrix. For example, FIG. 17 shows a series of exemplary images showing healing of a wound generated in a nude (hairless) mouse, where micrografts obtained from the skin of a black mouse were implanted in the wound area and the wound was then allowed to heal. After about 6 weeks, the wound appears to be well-healed, and some tufts of black hair are observable. The appearance of these tufts of black hair on the nude recipient site suggest that at least some of the micrografts survived during the healing process and that functional hair follicles were successfully transplanted to the nude recipient.

Figure 18A:
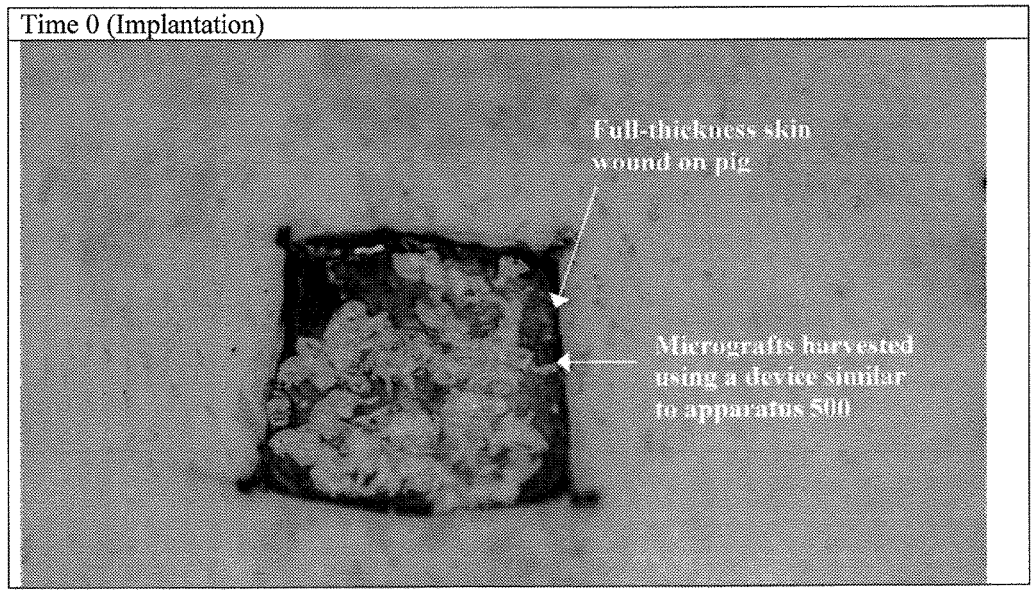
FIG. 18A is an exemplary image of a full-thickness skin wound formed in a swine subject.

FIG. 18A shows an exemplary wound formed in a swine subject by surgically removing a substantially square region of full-thickness skin tissue (epidermis and dermis, down to the subcutaneous fat layer). The size of this wound is approximately 1.5 cm×1.5 cm. Micrografts were harvested from a donor site of the swine subject using a device similar to the apparatus 500 shown in FIG. 5A, in accordance with the exemplary embodiments described herein. The micrografts were implanted directly into one such wound (without using a matrix). A second similar wound was also generated in the subject and allowed to heal without implantation of any micrografts.

Figure 18B:
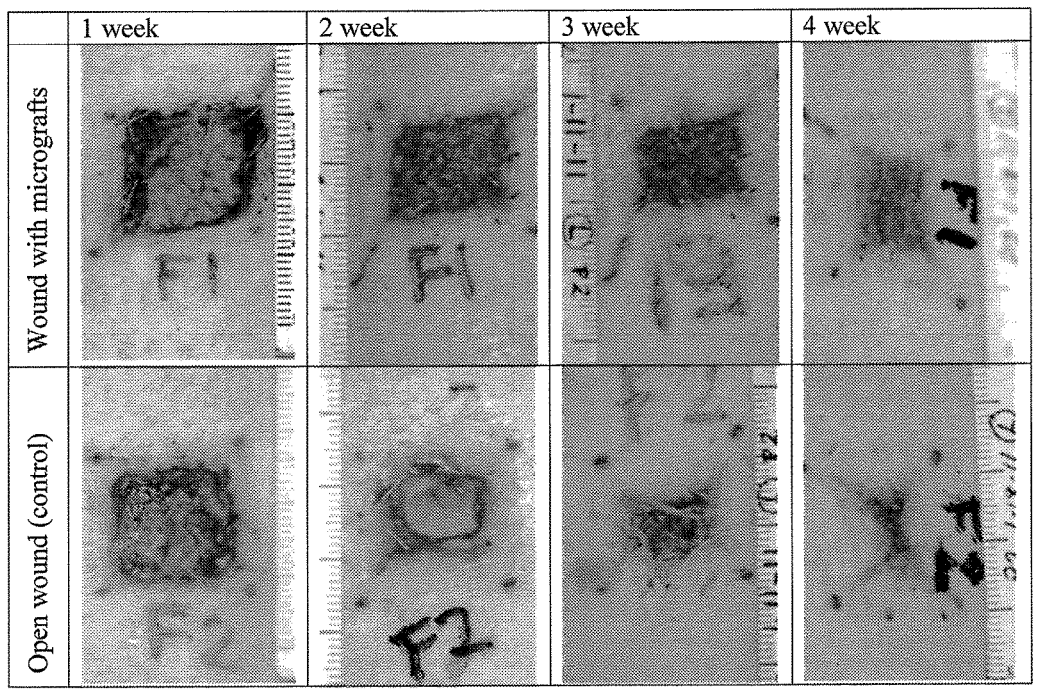
FIG. 18B is a series of exemplary images showing healing progress of an exemplary wound as shown in FIG. 18A with and without implanted micrografts.

The upper row of FIG. 18B illustrates a series of exemplary images showing the healing progress over 4 weeks for the wound shown in FIG. 18A that had micrografts implanted therein. The lower row of FIG. 18B are exemplary images showing the healing progress over 4 weeks for the wound that had no micrografts. The amount of observed wound contraction appears substantially reduced in the wound that had micrografts implanted in the wound site. In contrast, the wound without micrografts appears to have contracted more significantly during the healing process. Contraction of skin tissue as a wound heals is generally undesirable. For example, contraction of the skin around a joint can reduce the range of motion of the joint and may also be painful when the joint is flexed or extended. In severe cases, the joint may be rendered substantially or completely immobile (e.g., severe tissue contraction around the temporomandibular joints may prevent opening of a subject's mouth, and may require a liquid diet). Accordingly, the implantation of micrografts into a wound area as described herein may reduce tissue contraction during wound healing and thereby reduce or avoid detrimental side effects of such contraction.

The exemplary methods and apparatus described herein can also be used to harvest other types of biological tissue using the exemplary methods and apparatus described herein, and need not be limited to skin. Embodiments of the present disclosure can facilitate harvesting of small tissue portions (e.g. micrografts 120) from various organs or tissue types while reducing or avoiding generation of damage in the donor site. The harvested tissue portions can provide viable tissue that may be used in various grafting or cultivation procedures.

The foregoing merely illustrates the principles of the present disclosure. Various modifications and alterations to the described embodiments will be apparent to those skilled in the art in view of the teachings herein. Various exemplary embodiments described herein can be used with one another interchangeably. It will thus be appreciated that those skilled in the art will be able to devise numerous techniques which, although not explicitly described herein, embody the principles of the present disclosure and are thus within the spirit and scope of the present disclosure. All patents and publications cited herein are incorporated herein by reference in their entireties.

What is claimed is:

1. A method for obtaining at least one portion of at least one biological tissue, comprising:
    providing a matrix material over a donor tissue site;
    positioning a distal end of at least one hollow tube proximal to the upper surface of the matrix material;
    positioning a pin within a lumen of the at least one tube such that the distal end of the pin is proximal to the distal end of the at least one tube;
    lowering the pin and the at least one tube together substantially through a thickness of the matrix material, such that the distal ends of the at least one tube and the pin are proximal to the surface of the donor tissue site;
    advancing the at least one tube into the donor site to sever the at least one portion of the at least one biological tissue from a surrounding tissue, wherein the distal end of the pin remains proximal to the surface of the donor tissue site;
    raising the at least one tube and the pin simultaneously at substantially the same rate until the distal end of the at least one tube is proximal to a lower surface of the matrix material; and
    retracting the at least one tube from the matrix while maintaining a location of the pin substantially stationary relative to the matrix material, such that the at least one portion of the at least one biological tissue remains within the matrix material.

2. The method of claim 1, further comprising providing at least one growth factor in the matrix material.

3. The method of claim 1, wherein the matrix material comprises at least one of collagen, low-melting agarose, or devitalized biological tissue.

* * * * *

UNITED STATES PATENT AND TRADEMARK OFFICE
CERTIFICATE OF CORRECTION

| | | |
|---|---|---|
| PATENT NO. | : 9,895,162 B2 | Page 1 of 1 |
| APPLICATION NO. | : 14/711936 | |
| DATED | : February 20, 2018 | |
| INVENTOR(S) | : Richard Rox Anderson et al. | |

It is certified that error appears in the above-identified patent and that said Letters Patent is hereby corrected as shown below:

In the Specification

Please insert the following after the first paragraph in Column 1, Line 3:
--STATEMENT REGARDING FEDERALLY SPONSORED RESEARCH
This invention was made with government support under W911NF-10-0017 awarded by the Defense Advanced Research Projects Agency. The government has certain rights in the invention.--.

Signed and Sealed this
Ninth Day of May, 2023

Katherine Kelly Vidal
*Director of the United States Patent and Trademark Office*